(12) United States Patent
Bigio et al.

(10) Patent No.: US 8,406,861 B2
(45) Date of Patent: Mar. 26, 2013

(54) DETECTING OPTICAL PROPERTIES OF A TURBID MEDIUM

(75) Inventors: Irving J. Bigio, Chestnut Hill, MA (US); Roberto Reif, Seattle, WA (US); Ousama A'Amar, Dedham, MA (US)

(73) Assignee: Trustees of Boston University, Boston, MA (US)

( * ) Notice: Subject to any disclaimer, the term of this patent is extended or adjusted under 35 U.S.C. 154(b) by 347 days.

(21) Appl. No.: 12/593,016

(22) PCT Filed: Mar. 28, 2008

(86) PCT No.: PCT/US2008/058743
§ 371 (c)(1),
(2), (4) Date: Sep. 25, 2009

(87) PCT Pub. No.: WO2008/121871
PCT Pub. Date: Oct. 9, 2008

(65) Prior Publication Data
US 2010/0042005 A1     Feb. 18, 2010

Related U.S. Application Data

(60) Provisional application No. 60/920,410, filed on Mar. 28, 2007.

(51) Int. Cl.
*A61B 5/00* (2006.01)
(52) U.S. Cl. .................................. 600/478; 600/476
(58) Field of Classification Search .............. 385/12; 600/176, 476, 478; 606/15
See application file for complete search history.

(56) References Cited

U.S. PATENT DOCUMENTS

| | | | | | |
|---|---|---|---|---|---|
| 4,566,438 | A | * | 1/1986 | Liese et al. | 600/176 |
| 5,104,392 | A | * | 4/1992 | Kittrell et al. | 606/15 |
| 6,571,118 | B1 | * | 5/2003 | Utzinger et al. | 600/476 |
| 6,850,656 | B1 | * | 2/2005 | Bevilacqua et al. | 385/12 |
| 2005/0002031 | A1 | | 1/2005 | Kraemer et al. | |
| 2010/0042005 | A1 | * | 2/2010 | Bigio et al. | 600/476 |

FOREIGN PATENT DOCUMENTS

| | | |
|---|---|---|
| WO | 92/14399 A | 9/1992 |
| WO | 00/20843 | 4/2000 |

OTHER PUBLICATIONS

Zonios, et al. "Modeling diffuse reflectance from semi-infinite turbid media: application to the study of skin optical properties," Optics Express 14(19): 8661-8674 (Sep. 18, 2006).

A'Amar et al., Journal of Biomedical Optics, 9(6):1320-1326 (2004). "Comparison between ultraviolet-visible and near-infrared elastic scattering spectroscopy of chemically induced melanomas in an animal model."

Bevilacqua et al., Applied Optics, 38(22):4939-4950 (1999). "In vivo local determination of tissue optical properties: applications to human brain."

(Continued)

*Primary Examiner* — Brian Casler
*Assistant Examiner* — Serkan Akar
(74) *Attorney, Agent, or Firm* — Nixon Peabody LLP; Ronald I. Eisenstein; Mark J. FitzGerald

(57) ABSTRACT

A device for measuring light scattering and absorption properties of a tissue, the device comprising: a probe comprising first and second optical fibers for irradiation and detection. The optical fibers are substantially parallel to each other at the distal end, and are separated by a distance of less than 2 mm, wherein said first and second optical fibers are arranged in said probe at an angle, 6=10 deg. to 45 deg., to the plane perpendicular to the distal end of said probe and wherein the tips of the optical fibers at the distal end are polished parallel to the plane perpendicular to the distal end of said probe.

14 Claims, 11 Drawing Sheets

OTHER PUBLICATIONS

Bigio and Mourant, Phys Med Biol, 42:803-814 (1997). "Ultraviolet and visible spectroscopies for tissue diagnostics: fluorescence spectroscopy and elastic-scattering spectroscopy."

Bigio et al., SPIE, 5141:142-146 (2003). "Elastic scattering spectroscopy for detection of prostate cancer: preliminary feasibility study."

Bigio and Bown, Cancer Biology & Therapy, 3(3):259-267 (2004). "Spectroscopic sensing of cancer and cancer therapy."

Doornbos et al., Phys Med Biol, 44:967-981 (1999). "The determination of in vivo human tissue optical properties and absolute chromophore concentrations using spatially resolved steady-state diffuse reflectance spectroscopy."

Farrell and Patterson, Med Phys, 19(4):879-888 (1992). "A diffusion theory model of spatially resolved, steady-state diffuse reflectance for the noninvasive determination of tissue optical properties in vivo."

Hayakawa et al., Applied Optics, 43(24):4677-4684 (2004). "Use of the delta-P1 approximation for recovery of optical absorption, scattering, and asymmetry coefficients in turbid media."

Kienle and Patterson, J Opt Soc Am, 14(1):246-254 (1997). "Improved solutions of the steady-state and the time-resolved diffusion equations for reflectance from a semi-infinite turbid medium."

Lovat et al., Gut, 55:1078-1083 (2006). "Elastic scattering spectroscopy accurately detects high grade dysplasia and cancer in Barrett's oesophagus."

Mirabal et al., Journal of Biomedical Optics, 74:587-594 (2002). "Reflectance spectroscopy for in vivo detection of cervical precancer."

Moffitt and Prahl, IEEE Journal, 7(6):952-958 (2001). "Sized-fiber reflectometry for measuring local optical properties."

Myakov et al., Journal of Biomedical Optics, 7(3):388-397 (2002). "Fiber optic probe for polarized reflectance spectroscopy in vivo: design and performance."

Pfefer et al., Journal of Biomedical Optics, 8(2):206-215 (2003). "Reflectance-based determination of optical properties in highly attenuating tissue."

Utzinger and Richards-Kortum, Journal of Biomedical Optics, 8(1):121-147 (2003). "Fiber optic probes for biomedical optical spectroscopy."

Wang et al., Journal of Biomedical Optics, 10(4):044017-1-17 (2005). "Depth-sensitive reflectance measurements using obliquely oriented fiber probes."

Zhu et al., Journal of Biomedical Optics, 8(2):237-247 (2003). "Effect of fiber optic probe geometry on depth-resolved fluorescence measurements from epithelial tissues: a Monte Carlo simulation."

Amelink, A. and Sterenborg, H.J.C.M., Applied Optics, 43(15):3048-3054 (2004). "Measurement of the local optical properties of turbid media by differential path-length spectroscopy."

Amelink, A. and Sterenborg, H.J.C.M., Applied Optics, 29(10):1087-1089 (2004). "In vivo measurement of the local optical properties of tissue by use of differential path-length spectroscopy."

Arifler, D. et al., Applied Optics, 44(20):4291-4305 (2005). "Reflectance spectroscopy for diagnosis of epithelial precancer: model-based analysis of fiber-optic probe designs to resolve spectral information from epithelium and stroma."

Dunn, A. and Boas, D., Optics Letters, 25(24):1777-1779 (2000). "Transport-based image reconstruction in turbid media with small source-detector separations."

Hayakawa, C.K. and Spanier, J., 26(17):1335-1337 (2001). "Perturbation Monte Carlo methods to solve inverse photon migration problems in heterogeneous tissues."

Johns, M. et al., Optics Express, 13(13):4828-4842 (2005). "Determination of reduced scattering coefficient of biological tissue from a needle-like probe."

Lin, S-P. et al., Applied Optics, 36(1):136-143 (1997). "Measurement of tissue optical properties by the use of oblique-incidence optical fiber reflectometry."

Liu, Q. and Ramanujam, N., Applied Optics, 45(19):4776-4790 (2006). "Sequential estimation of optical properties of a two-layered epithelial tissue model from depth-resolved ultraviolet-visible diffuse reflectance spectra."

Nieman, L. et al., Applied Optics, 43(6):1308-1319 (2004). "Optical sectioning using a fiber probe with an angled illumination-collection geometry: evaluation in engineered tissue phantoms."

Palmer, G.M. and Ramanujam, N., Applied Optics, 45(5):1062-1071 (2006). "Monte Carlo-based inverse model for calculating tissue optical properties. Part I: Theory and validation on synthetic phantoms."

Palmer, G.M. et al., Applied Optics, 45(5):1072-1078 (2006). "Monte Carlo-based inverse model for calculating tissue optical properties. Part II: Application to breast cancer diagnosis."

Pfefer, T.J. et al., Applied Optics, 41(22):4712-4721 (2002). "Multiple-fiber probe design for fluorescence spectroscopy in tissue."

Reif, R. et al., Applied Optics, 46(29):7317-7328 (2007). "Analytical model of light reflectance for extraction of the optical properties in small volumes of turbid media."

Sun, J. et al., Applied Optics, 45(31):8152-8162 (2006). "Influence of fiber optic probe geometry on the applicability of inverse models of tissue reflectance spectroscopy: computational models and experimental measurements."

Zonios, G. et al., Applied Optics, 38(31):6628-6637 (1999). "Diffuse reflectance spectroscopy of human adenomatous colon polyps in vivo."

Zonios, G. and Dimou, A., Optics Express, 14(19):8661-8674 (2006). "Modeling diffuse reflectance from semi-infinite turbid media: application to the study of skin optical properties."

* cited by examiner

DETECTING OPTICAL PROPERTIES OF A TURBID MEDIUM

CROSS-REFERENCE TO RELATED APPLICATIONS

The present application is a 35 U.S.C. §371 National Stage of International Application No. PCT/US2008/058743 filed on Mar. 28, 2008, which designates the United States, and which claims the benefit of priority under 35 U.S.C. §119(e) of U.S. Provisional Application Ser. No. 60/920,410 filed on Mar. 28, 2007, the contents of which are herein incorporated by reference in its entirety.

GOVERNMENT SUPPORT

This invention was made with Government support under grant numbers U54 CA104677-01 and F31 CA110016 awarded by the National Institutes of Health. The Government has certain rights in this invention.

FIELD OF THE INVENTION

The present invention relates to detecting optical properties of a turbid medium. The invention also relates to extracting optical properties from data obtained from biological tissue.

BACKGROUND

An important challenge in biomedical research is to non-invasively characterize tissue conditions, for the purposes of diagnosis of disease, such as (pre)cancerous conditions, or for monitoring response to treatment. Non-invasive optical reflectance measurements have been used to extract diagnostic information from a variety of tissue types, in vivo, such as colon[49], skin[50], brain[51], cervix[52], esophagus[53], prostate[54] and bronchial mucosa[55]. The experimental setup of these systems often consists of a fiber probe with a diameter of a few millimeters or less, with one or more fibers that transmit light to and from the tissue. These in situ measurements of the optical properties of a tissue can reveal information concerning the morphological and biochemical composition of the tissue. Optical techniques are also used in vivo to identify changes that occur in biological tissues[1-3] associated with disease progression.

Tissues can be characterized by their optical properties, which are defined by the absorption coefficient ($\mu_a$), the scattering coefficient ($\mu_s$), the phase function ($p(\theta)$), the anisotropy value ($g=<\cos\theta>$) and the reduced scattering coefficient ($\mu_s'=\mu_s(1-g)$). The diffusion approximation to the Boltzman transport equation is a method that has been used successfully to determine the absorption coefficient and the reduced scattering coefficient in turbid media[4-6]. The validity of the diffusion approximation is limited to media with higher scattering than absorption ($\mu_s'>>\mu_a$), which is satisfied in biological tissues for the wavelength region between 600-900 nm, and to large separations between the source and the detector ($\rho>>1/\mu_s'$). As a consequence, the collected photons travel through a large volume of tissue, and the extracted optical properties represent average values for the tissue volume probed. However, many clinical settings require small fiber probes (e.g. endoscope working channels typically have a diameter of <3 mm). Different methods have been used to determine the optical properties in turbid media at small source-detector separations[7-19], including some based on the diffusion approximation[20,21]. Various fiber optic probe designs have been developed for reflectance and fluorescence measurements[22-25]. In many applications the tissues of interest are thin. Most cancers arise in the epithelium, which is a superficial tissue layer with a thickness, typically, of 100-500 micrometers. Hence, sensitivity to the optical properties of the epithelial layer requires superficial measurement techniques. The penetration depth of the collected photons depends on the fiber probe geometry and the optical properties of the sample[16,24,26,27], which may allow the interrogation depth to extend beyond the epithelial layer.

SUMMARY OF THE INVENTION

The invention provides methods and devices for evaluating the optical properties of turbid media. In this context, a turbid medium is one which both absorbs and scatters light. Turbid media of particular interest include fluids, such as water or other liquids with suspended particulates, industrially relevant fluids such as coolants, paints, etc., and biologically or medically relevant fluids, such as blood, culture media, etc. An important turbid medium of interest is tissue, and particularly epithelial layers of tissue. Measurement of changes in the optical properties of any turbid medium can provide valuable information. Changes or differences in the optical properties of tissue, including epithelial layers of tissue can provide indicia of pathological state or the efficacy of a therapeutic regimen. In general, the change or difference can be a change or difference relative to a standard that is either internal or external.

Provided herein are methods for obtaining absolute values for optical properties that are generally only obtained as relative values. Whereas relative values are of somewhat limited use in that they do not readily translate to comparisons with other samples, an absolute value can be compared effectively with an absolute value from another sample with meaningful results.

In one aspect, described herein is device for measuring light scattering and absorption properties of a tissue, the device comprising: a probe having proximal and distal ends, the probe comprising first and second optical fibers, wherein the first optical fiber is operatively connected to a light source, and the second optical fiber is operatively connected to an optical detector, wherein the first and the second optical fibers are substantially parallel to each other at the distal end, and are separated at the distal end by a distance of less than 2 mm, wherein the first and second optical fibers are arranged in the probe at an angle, $\theta=10°$ to $45°$, to the plane perpendicular to the distal end of the probe and wherein the tips of the optical fibers at the distal end are polished parallel to the plane perpendicular to the distal end of the probe.

In one embodiment of this and all other aspects described herein, the probe comprises an endoscopic probe.

In another embodiment of this and all other aspects described herein, the device comprises, or the method uses a device comprising a computer-readable medium comprising instructions for obtaining an absolute reflectance value from a measured reflectance spectrum, the medium comprising: a) instructions for receiving a value for measured light energy from a turbid medium of interest; b) instructions for receiving values for measured light energy from a calibration turbid medium of known reflectance and absorption properties; c) instructions for calculating an absolute reflectance value, R for the turbid medium of interest, the instructions comprising applying the values received according to instructions (a) and (b) to the relationship of Equation (1)

$$R = \frac{S_P(\lambda)}{S_C(\lambda)} R_C(\lambda) \qquad \text{Equation (1)}$$

wherein $S_p(\lambda)$ is the reflected light energy detected from the turbid medium, $S_c(\lambda)$ is the reflected light energy detected from a turbid medium with known reduced scattering and/or absorption coefficients, and $R_c(\lambda)$ is the reflectance from the turbid medium with known reduced scattering and/or absorption coefficients; and d) instructions for transmitting a value for R to an output device.

In another embodiment of this and all other aspects described herein, the device comprises or the method uses a device comprising a computer-readable medium that further comprises: instructions for determining absorption and/or reduced scattering coefficients for the turbid medium of interest by applying the relationship of Equation (2) to the absolute reflectance value, R $$R = (a\mu_s')\exp\left(-\mu_a \frac{b}{(\mu_a \mu_s')^c}\right) \qquad \text{Equation (2)}$$

wherein a, b, and c are constants, $\mu_s'$ is the reduced scattering coefficient of the turbid medium of interest, and $\mu_a$ is the absorption coefficient of the turbid medium of interest; and instructions for transmitting a value of $\mu_s'$ and/or $\mu_a$ to an output device.

In another embodiment of this and all other aspects described herein, the constants a, b, and c are 0.1, 0.2, and 0.2, respectively.

In another embodiment of this and all other aspects described herein, the first and second optical fibers are separated by less than or equal to 700 μm at the distal end of the probe. In further embodiments of this and all other aspects described herein, the first and second optical fibers are separated by less than or equal to 500 μm, less than or equal to 200 μm at the distal end of the probe, including all distances between 200 μm and zero as if specifically recited here, inclusive of zero—i.e., the first and second optical fibers can be in contact with each other at the distal end of the probe.

In another aspect, a method is described for measuring reflectance, light scattering and/or absorption properties of a turbid medium, the method comprising: a) contacting a turbid medium of interest with the distal ends of first and second optical fibers comprised by a probe, the first optical fiber operatively connected to a light source, and the second optical fiber operatively connected to an optical detector, wherein the first and the second optical fibers are substantially parallel to each other and are separated at their distal ends by a distance of less than 2 mm, and wherein the first and second optical fibers are arranged in the probe at an angle, θ=10° to 45°, to the plane perpendicular to the distal end of the probe; b) irradiating the turbid medium with light from the first optical fiber; c) collecting light reflected from the turbid medium with the second optical fiber and measuring the collected reflected light spectra with the detector; and d) determining reflectance, and/or light absorption or scattering coefficients for the turbid medium based on the amount of light measured at the detector.

In one embodiment of this and all other aspects described herein, the turbid medium comprises a tissue. In another embodiment of this and all other aspects described herein, the tissue can be an epithelial layer, including an epithelial layer of a subject.

In another embodiment of this and all other aspects described herein, the measurements permitted by the methods and devices described can be used for the diagnosis of disease. In alternative embodiments of this and all other aspects described herein, the methods and devices are not used for the diagnosis of disease.

In another embodiment of this and all other aspects described herein, the turbid medium comprises a solvent, an environmental water sample, an industrial water sample, biological fluid, an industrial liquid, a coolant, a lubricant, milk, paint, or a liquid fuel.

In another embodiment of this and all other aspects described herein, method further comprises standardizing the reflectance with reference data obtained by applying Equation (1) to reflectance data obtained from a calibrating turbid medium having known values of absorption and/or reduced scattering coefficient, $$R = \frac{S_P(\lambda)}{S_C(\lambda)} R_C(\lambda) \qquad \text{Equation (1)}$$

wherein $S_p(\lambda)$ is the reflected light spectra detected from the turbid medium, $S_c(\lambda)$ is the reflected light spectra detected from a calibrating turbid medium with known reduced scattering and/or absorption coefficients, $R_c(\lambda)$ is the reflectance from the calibrating turbid medium with known reduced scattering and/or absorption coefficients; and wherein the standardizing provides absolute values for reflectance spectra from measured reflectance spectra.

In another embodiment of this and all other aspects described herein the method further comprises the step of determining a reduced scattering coefficient and/or an absorption coefficient for the turbid medium of interest, wherein the determining comprises applying Equation (2) to the absolute reflectance value, R $$R = (a\mu_s')\exp\left(-\mu_a \frac{b}{(\mu_a \mu_s')^c}\right) \qquad \text{Equation (2)}$$

wherein a, b, and c are constants, $\mu_s'$ is the reduced scattering coefficient of the turbid medium of interest, and $\mu_a$ is the absorption coefficient of the turbid medium of interest.

In another embodiment of this and all other aspects described herein, the step of determining light absorption and/or scattering coefficients comprises determining an absolute value of reflectance, R, by contacting a calibrating turbid medium having known reduced scattering and absorption coefficients with the probe, irradiating the calibrating turbid medium with light energy from the first optical fiber, collecting and detecting light reflected from the calibrating turbid medium via the second optical fiber, and applying the relationship of Equation (1) to the amount of reflected light detected in step (c) to determine the absolute reflectance value, R $$R = \frac{S_P(\lambda)}{S_C(\lambda)} R_C(\lambda) \qquad \text{Equation (1)}$$

wherein $S_p(\lambda)$ is the reflected light spectra detected from the turbid medium, $S_c(\lambda)$ is the reflected light spectra detected from a turbid medium with known reduced scattering and/or absorption coefficients, and $R_c(\lambda)$ is the reflectance from the turbid medium having known reduced scattering and absorption coefficients.

In another embodiment of this and all other aspects described herein, the step of determining light absorption and/or scattering coefficients comprises applying the relationship of Equation (2) to the absolute reflectance value, R $$R = (a\mu_s')\exp\left(-\mu_a \frac{b}{(\mu_a \mu_s')^c}\right) \quad \text{Equation (2)}$$

wherein a, b, and c are constants, $\mu_s'$ is the reduced scattering coefficient, and $\mu_a$ is the absorption coefficient.

In another embodiment of this and all other aspects described herein, the tips of the optical fibers at the distal end of the probe are polished parallel to the plane perpendicular to the distal end of the probe.

In another embodiment of this and all other aspects described herein, the method further comprises the step of comparing reflectance, and/or light absorption or scattering coefficients obtained from the turbid medium with the reflectance, and/or light absorption or scattering coefficients obtained from a reference turbid medium.

In another embodiment of this and all other aspects described herein, the depth of a tissue from which reflected light is measured is less than or equal to about 500 µm.

In another aspect, described herein is a method of obtaining an absolute value for reflectance from spectra reflected from a turbid medium of interest, the method comprising: a) irradiating a first turbid medium with light energy from a source in contact with the first turbid medium, the first turbid medium having known reduced scattering and absorption coefficients; b) for the first turbid medium, measuring an amount of light energy reflected from the source to a detector; c) irradiating a turbid medium of interest with light energy from a source in contact with the turbid medium of interest; d) collecting and detecting the amount of light energy from the source that is reflected to a detector from the turbid medium of interest, e) applying measured data representing the amounts of light energy reflected from the first turbid medium having known reduced scattering and absorption coefficients, and measured data representing the amount of light energy reflected from the turbid medium of interest to Equation (1):

$$R = \frac{S_P(\lambda)}{S_C(\lambda)} R_C(\lambda) \quad \text{Equation (1)}$$

wherein $S_p(\lambda)$ is the reflected light spectra detected from the turbid medium of interest, $S_c(\lambda)$ is the reflected light spectra detected from the turbid medium with known reduced scattering and/or absorption coefficients, $R_c(\lambda)$ is the reflectance from the first turbid medium with known reduced scattering and/or absorption coefficients; and wherein an absolute value for the reflectance, R, from the turbid medium of interest is obtained.

In another embodiment of this and all other aspects described herein, method further comprises the step of determining a reduced scattering coefficient and/or an absorption coefficient for the turbid medium of interest, wherein the determining comprises applying Equation (2) to the absolute reflectance value, R $$R = (a\mu_s')\exp\left(-\mu_a \frac{b}{(\mu_a \mu_s')^c}\right) \quad \text{Equation (2)}$$

wherein a, b, and c are constants, $\mu_s'$ is the reduced scattering coefficient, and $\mu_a$ is the absorption coefficient. In another embodiment of this and all other aspects described herein, the constants a, b, and c are 0.1, 0.2, and 0.2, respectively.

In another embodiment of this and all other aspects described herein, the method further comprises the step of comparing the absolute reflectance value, R, to an absolute reflectance value obtained from a reference turbid medium, wherein a difference between the absolute reflectance values is indicative of a difference between the turbid medium of interest and the reference turbid medium.

In another embodiment of this and all other aspects described herein, the method further comprises the step of comparing an absolute value for the reduced scattering or absorption coefficient of the turbid medium of interest to a reduced scattering coefficient and/or absorption coefficient obtained from a reference turbid medium, wherein a difference in the absolute value is indicative of a difference between the turbid medium of interest and the reference turbid medium.

In another embodiment of this and all other aspects described herein, the turbid medium of interest and the reference turbid medium are each an epithelial layer, and a difference in the absolute value is indicative of a physiological difference between the epithelial layer in the sample of interest and the reference. The physiological difference can be indicative of a disease state. The methods and devices described herein are well suited for the situation in which a test determination of optical properties of a tissue provide absolute values that can be compared to standards to provide a direct diagnostic tool, i.e., an indicator of disease. The indicator can either point directly to a disease state—i.e., no further testing is required, or, alternatively, can provide information suggestive of a disease state, i.e., an indication that further, potentially more invasive testing is warranted, such as a biopsy. Better correlations between differences in optical properties and disease state can be gained where a larger number of samples are examined to establish both healthy and disease tissue (e.g., cancer, irritable bowel syndrome, inflammatory disease, Crohn's disease, cervical disease, etc.) standards. Many diseases are correlated with the optical properties (scattering and absorption) of tissue. The scattering is dependent on the morphological composition of cell scattering centers, such as nucleus, mitochondria and other organelles. The absorption is dependent on the concentration of several endogenous compounds such as hemoglobin, bilirubin and cytochrome oxidase, and exogenous compounds such as several chemotherapy and photodynamic therapy agents. Most cancers originate in the epithelium (a superficial tissue layer with a thickness of 100-500 µm) of organs such as the esophagus, skin and urinary bladder. A standard or set of standards based on a large sample size can thus provide a more reliable diagnostic criterion for comparison. When a test sample varies from a normal sample in a degree to which a known disease sample or standard does, the test can correlate very accurately with disease diagnosis. Thus the degree of variation that is considered a "difference" will generally depend upon the sample size of the reference or standard, with larger sample numbers for both standard tissues (i.e., known healthy or known diseased) and test tissues providing more sensitive results.

In another aspect, described herein is a method of measuring reflectance spectra from a turbid medium of interest, the method comprising obtaining reflectance spectra from a turbid medium of interest using a probe in contact with the turbid medium of interest, the probe operatively connected to a light energy source which irradiates the turbid medium of interest and an optical detector which detects light energy reflected from the turbid medium of interest, and standardizing the reflectance data with reference data obtained by applying Equation (1) to reflectance data obtained from a calibrating turbid medium having known values of absorption and/or reduced scattering coefficient, $$R = \frac{S_P(\lambda)}{S_C(\lambda)} R_C(\lambda) \qquad \text{Equation (1)}$$

wherein $S_p(\lambda)$ is the reflected light spectra detected from the turbid medium, $S_c(\lambda)$ is the reflected light spectra detected from a calibrating turbid medium with known reduced scattering and/or absorption coefficients, $R_c(\lambda)$ is the reflectance from the calibrating turbid medium with known reduced scattering and/or absorption coefficients; and wherein the standardizing provides absolute values for the reflectance spectra from measured reflectance spectra.

In another embodiment of this and all other aspects described herein, the method further comprises the step of determining a reduced scattering coefficient and/or an absorption coefficient for the turbid medium of interest, wherein the determining comprises applying Equation (2) to the absolute reflectance value, R $$R = (a\mu_s')\exp\left(-\mu_a \frac{b}{(\mu_a\mu_s')^c}\right) \qquad \text{Equation (2)}$$

wherein a, b, and c are constants, $\mu_s'$ is the reduced scattering coefficient of the turbid medium of interest, and $\mu_a$ is the absorption coefficient of the turbid medium of interest.

In another embodiment of this and all other aspects described herein, the method further comprises the step of comparing the absolute reflectance value, R, to an absolute reflectance value obtained from a reference turbid medium, wherein a difference between the absolute reflectance values is indicative of a difference between the turbid medium of interest and the reference turbid medium.

In another embodiment of this and all other aspects described herein, the method further comprises the step of comparing an absolute value for the reduced scattering or absorption coefficient of the turbid medium of interest to a reduced scattering coefficient and/or absorption coefficient obtained from a reference turbid medium, wherein a difference in the absolute value is indicative of a difference between the turbid medium of interest and the reference turbid medium.

In another embodiment of this and all other aspects described herein, the turbid medium of interest and the reference turbid medium are each an epithelial layer, and a difference in the absolute value is indicative of a disease state.

In another aspect, a method is described for diagnosing a disease, the method comprising: a) contacting a tissue of interest with the distal ends of first and second optical fibers comprised by a probe, the first optical fiber operatively connected to a light source, and the second optical fiber operatively connected to an optical detector, wherein the first and the second optical fibers are substantially parallel to each other and are separated at their distal ends by a distance of less than 2 mm, and wherein the first and second optical fibers are arranged in the probe at an angle, θ=10° to 45°, to the plane perpendicular to the distal end of the probe; b) irradiating the tissue with light from the first optical fiber; c) collecting light reflected from the tissue with the second optical fiber and measuring the collected reflected light spectra with the detector; and d) determining reflectance, and/or light absorption or scattering coefficients for the tissue based on the amount of light measured at the detector, e) comparing the reflectance, and/or light absorption or scattering coefficients for the tissue with a standard, wherein a difference in one or more of the reflectance, and/or light absorption or scattering coefficient relative to the standard is indicative of a disease state.

In another embodiment of this and all other aspects described herein, the method further comprises standardizing the reflectance with reference data obtained by applying Equation (1) to reflectance data obtained from a calibrating reference medium having known values of absorption and/or reduced scattering coefficient, $$R = \frac{S_P(\lambda)}{S_C(\lambda)} R_C(\lambda) \qquad \text{Equation (1)}$$

wherein $S_p(\lambda)$ is the reflected light spectra detected from the tissue, $S_c(\lambda)$ is the reflected light spectra detected from a calibrating reference with known reduced scattering and/or absorption coefficients, $R_c(\lambda)$ is the reflectance from the calibrating reference medium with known reduced scattering and/or absorption coefficients; wherein the standardizing provides absolute values for reflectance spectra from measured reflectance spectra, and wherein the comparing compares the absolute reflectance from the tissue to an absolute reflectance value from another tissue.

In another embodiment of this and all other aspects described herein, the method further comprises the step of determining a reduced scattering coefficient and/or an absorption coefficient for the tissue, wherein the determining comprises applying Equation (2) to the absolute reflectance value, R $$R = (a\mu_s')\exp\left(-\mu_a \frac{b}{(\mu_a\mu_s')^c}\right) \qquad \text{Equation (2)}$$

wherein a, b, and c are constants, $\mu_s'$ is the reduced scattering coefficient of the tissue, and $\mu_a$ is the absorption coefficient of the tissue.

As used herein, the term "substantially parallel," when used in reference to optical fibers, means that the fibers are, at their distal ends, aligned to within at least 3 degrees or less of parallel, preferably within at least 2 degrees of parallel, preferably within at least 1 degree of parallel, more preferably within 0.5 degrees or less of parallel.

Figure 1:
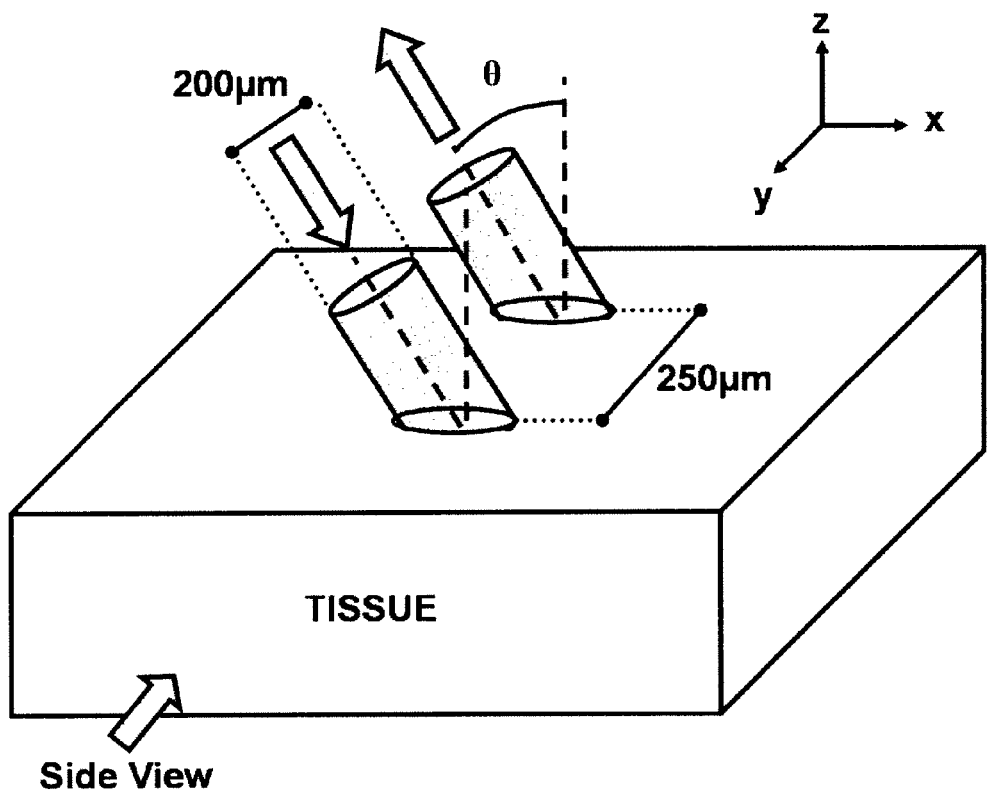
FIG. 1 Diagram of a fiber probe design used in both Monte Carlo simulations and experiments in tissue media.

Table 1. Values for the coefficients a and a0 obtained with Monte Carlo simulations and experiments in tissue calibrating turbid media with a 0, 15, 30 and 45 degree fiber probe configuration.

Table 2. Values for the coefficient b obtained with Monte Carlo simulations and experiments in tissue calibrating turbid media with a 0, 15, 30 and 45 degree fiber probe configuration.

Table 3. Values for the coefficient c obtained with Monte Carlo simulations and experiments in tissue media with a 0, 15, 30 and 45 degree fiber probe configuration.

Table 4. Values for the coefficients a, a0, b and c obtained with Monte Carlo simulations with a 0 and 45 degree fiber probe configuration under different conditions. The gray boxes indicate the changes in the parameters referenced to the parameters described in column A. Further detail is provided herein in the Examples section. Table 5. Mean and standard deviation over fifteen measurements of the absorption coefficient extracted from experiments in tissue calibrating media with a 0, 15, 30 and 45 degree fiber probe configuration at 610m.

Table 6. Mean and standard deviation over fifteen measurements of reduced scattering coefficient extracted from experiments in tissue calibrating media with a 0, 15, 30 and 45 degree fiber probe configuration at 610 nm.

DETAILED DESCRIPTION

Many techniques have focused on making optical measurements in a geometry for which the diffusion approximation is applicable. The disadvantage of photon diffusion based techniques is that it requires large sampling volumes. In response to the need for methods that would measure optical properties at superficial layers, an alternate technique was developed. In situ measurements of scattering and absorption properties in turbid media has many applications in medicine and in the pharmacology industry.

Monte Carlo simulations and experiments in tissue media were used to empirically develop an analytical model that characterizes the reflectance spectrum in a turbid medium. The model extracts the optical properties (scattering and absorption coefficients) of the medium at small source-detector separations, for which the diffusion approximation is not valid. The accuracy of the model and the inversion algorithm were investigated and validated. Four fiber probe configurations were tested for which both the source and the detector fibers were tilted at a predetermined angle, with the fibers parallel to each other. This parallel-fiber geometry facilitates clinical endoscopic applications and ease of fabrication. Accurate extraction of tissue optical properties from in vivo spectral measurements could have potential applications in detecting, non-invasively and in real-time, epithelial (pre) cancers. In addition, reflectance measurements were obtained in vivo from mouse thigh muscle while varying the contact pressure of the fiber optic probe. It is determined that the probe pressure is a variable that affects the local optical properties of the tissue. The reflectance spectra were analyzed with an analytical model that extracts the tissue optical properties and facilitates the understanding of underlying physiological changes induced by the probe pressure.

Disclosed herein is a device with a probe design for which source and detector fibers are tilted with respect to the tissue surface but, unlike previous designs, the fibers are kept parallel in respect to each other as observed in FIG. 1. This type of fiber probe geometry offers benefits of convenience for clinical applications with endoscopes, and ease of fabrication. Also disclosed herein is an analytical model that can extract the absorption and scattering coefficients of a turbid medium using a small source-detector separation, based on analysis of the reflectance spectrum. Thus, the analytical model can be used for describing the reflectance of a scattering and absorbing medium in various biological and non-biological turbid media as described herein. The model is successful in describing a reflectance spectrum at small source-detector separations and is not limited to a parameter range with scattering much larger than absorption, a limitation that generally plagues models based on diffusion theory. In addition, the analytical model described herein can be used to determine absolute reflectance, reduced scattering coefficients, and absorption coefficients of a turbid medium. Provided herein are methods for obtaining absolute values for optical properties of a turbid medium. Whereas relative values are of somewhat limited use in that they do not readily translate to comparisons with other samples, an absolute value can be compared effectively with an absolute value from another sample with meaningful results.

While tilted fiber optic probes have been employed for controlling the depth of penetration in tissue spectroscopy applications[26-30] the applications are generally modeled after a diffusion based theory. An device and an analytical model for use with such tilted probes is disclosed herein, wherein the analytical model for use with the device is not bound by diffusion based theories. Described herein are Monte Carlo simulations, which indicate that tilting both the source and the detector optical fibers, such that the fibers are parallel to each other, enhances the sensitivity to superficial volumes of tissue, while maintaining a fiber-probe geometry that is convenient for clinical applications and is easy to fabricate. The model has been shown herein in the Examples section for fiber probe tilt angles between 0 and 45 degrees. The objective is to develop a diagnostic tool that can facilitate the determination of biologically relevant parameters such as size and size distribution of cellular organelles, tissue blood content and hemoglobin oxygen saturation. The model is developed and validated using Monte Carlo simulations and experiments with tissue calibrating media.

Also disclosed herein are methods for using the tilted probe (with a small source-detector distance) for determining the optical properties of biological tissue.

EXAMPLES

Example 1a

Exemplary Methods for Defining an Analytical Model Described Herein

A. Monte Carlo Simulations

A Monte Carlo (MC) code that simulates light transport within a scattering and absorbing medium has been developed based on previous codes[31,32], using a variance reduction technique[33]. The MC code simulates a probe that comprises two fibers (a source and a detector), as depicted in FIG. 1. Each fiber has a core diameter of 200 μm and a numerical aperture (NA) of 0.22 in air. The fibers have a center-to-center separation of 250 μm. Both fibers can be tilted at an angle ($\theta$) relative to the tissue surface normal, in the x-z plane, such that the fibers are parallel to each other. Four tilt angles have been investigated: 0, 15, 30 and 45 degrees. The surfaces of the fibers were modeled to be polished at an angle such that the faces of the fibers were parallel to the surface of the medium. Thus, the faces of the fibers had a circular or elliptical shape depending on whether $\theta=0$ or $\theta>0$, respectively. Photons were launched from points within the surface of the source fiber into the medium, with an angle within the NA and appropriate tilt angle of the fiber (including index mismatch correction). The launch point and angle of each photon were chosen by using a random uniform distribution. The propagation of photons within the medium was determined by the absorption coefficient, the scattering coefficient and the Henyey-Greenstein (HG)[34] or modified Henyey-Greenstein (MHG)[9,35] phase function. Unless otherwise indicated, throughout this application the HG phase function is used. Photons were terminated from the simulation when they had traveled farther than a specified distance from the source fiber, had a path-length larger than a specified value or left the surface of the medium. The specified distance and path-length values were selected such that they had a negligible effect on the results of the simulation. The simulation also accounts for reflection at the surface of the medium due to the mismatch of the index of refraction. Photons were collected when they arrived at the surface of the medium within the diameter, NA and tilt angle of the collection fiber. The index of refraction of the fibers and the medium were set to 1.5 and 1.4, respectively. Over two million photons were tracked per simulation.

Figure 2:
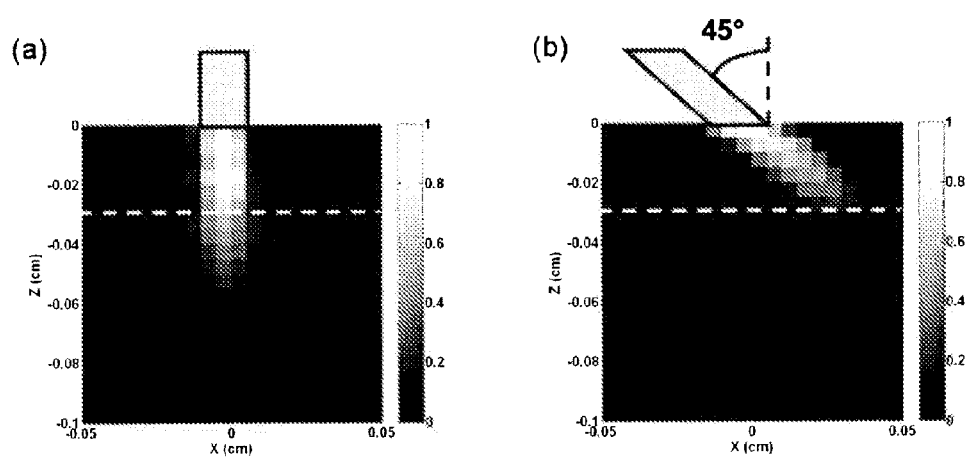
FIG. 2 Normalized voxel visitation history of a Monte Carlo simulation for (a) 0 degree and (b) 45 degree fiber probe configuration. The dotted line depicts a depth of 300 μm.

The paths of photons traveling from a source to a detector fiber depend on the optical properties of the medium and on the fiber probe geometry. When the fibers are tilted at an angle $\theta_f$, the light is bent inside the medium to an angle $\theta_m$, which is described by Snell's Law $n_f \sin \theta_f = n_m \sin \theta_m$, where $n_f$ and $n_m$ are the indices of refraction of the fiber and the medium, respectively. Since the index of the fiber is typically higher than the index of the medium, then $\theta_m > \theta_f$. FIG. 2 depicts the normalized voxel visitation history of the collected photons from a side view (as indicated in FIG. 1) for the 0 and 45 degree fiber probe configurations in a medium with $\mu_a=0.1$ cm$^{-1}$, $\mu_s'=10$ cm$^{-1}$ and g=0.9. The dotted white line represents a depth of 300 μm. It is observed that the 45 degree fiber probe configuration is more sensitive to collecting light in superficial volumes of tissue, compared to the 0 degree fiber probe configuration. It is important to note that the depth of penetration of the collected photons is also dependent on the optical properties of the tissue.

B. Instrumentation

The experimental set-up for the reflectance measurements comprised a pulsed Xenon-arc lamp (LS-1130-3, Perkin Elmer) as a broadband light source, a spectrometer (S2000, Ocean Optics, Inc.) and a fiber probe for the delivery and collection of the light to and from the sample. Four fiber probe configurations were fabricated with tilt angles of 0, 15, and 45 degrees, as depicted in FIG. 1. The probes had two multimode optical fibers (source and detector) which are parallel to each other. The center-to-center separation between the fibers was approximately 250 μm. Each optical fiber had a core diameter of 200 μm and a NA of 0.22 in air. The tips of the probes were polished parallel to the surface of the medium for each of the angles.

The tilt angles of the fiber probes were verified by inserting the angled tip in a dilute solution of titanium dioxide and water, and measuring the output angle of a HeNe (632.8 nm) laser. Snell's law was used to determine that the probes were within 1.5 degrees of the expected tilt angle.

C. Liquid Calibrating Media

Tissue Calibrating Turbid Media

Figure 3:
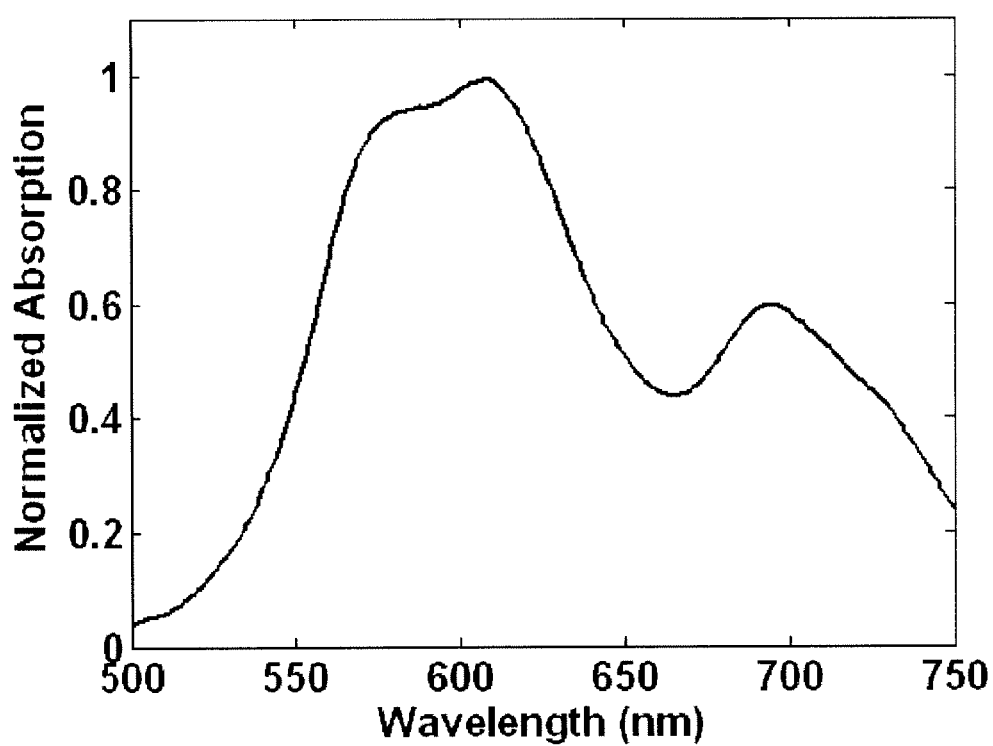
FIG. 3 An absorption spectrum of Indigo Blue dye normalized to the peak at 610 nm.

A calibrating liquid tissue turbid media (also referred to as "tissue media" or "tissue medium" or "tissue calibrating turbid media" herein) were prepared using deionized water, Intralipid-10% (Fresenius Kabi) as a source of scattering and Indigo Blue dye (Daler-Rowney) as an absorber. Intralipid-10% has been previously demonstrated to scatter light preferentially in the forward direction[36]. The wavelength-dependent extinction coefficient of the Indigo Blue dye was measured using a spectrophotometer (Varian, Cary-50), and the absorption spectrum, normalized to the peak at 610 nm, is shown in FIG. 3. The reduced scattering coefficients of the tissue media were determined using a method of spatially-dependent diffuse reflectance spectroscopy[37]. Known amounts of dye were added to the medium to obtain the appropriate absorption coefficient. It is important to note that the amount of dye solution added did not exceed 0.5% of the volume of the tissue medium; therefore, the alterations of the scattering properties were negligible. Unless otherwise indicated, the values of the reduced scattering coefficient and absorption coefficient discussed herein are at a wavelength of 610 nm. Each medium contained 200 ml of solution and was placed inside a cylindrical container.

Titanium Dioxide Calibration Medium

A calibration liquid medium was made by suspending 0.16 grams of titanium dioxide powder (J. T. Baker) in 200 ml of deionized water, and is referred to herein as "titanium dioxide calibration media", "calibration media" or "calibration medium". Titanium dioxide has an anisotropy value of about 0.5 in aqueous suspension[38]. No absorber was added to the calibration medium. The reduced scattering coefficient of the calibration medium was determined using the method of spatially-dependent diffuse reflectance spectroscopy[37].

D. Data Acquisition

Spectral measurements were obtained by subtracting a dark measurement (lamp was not fired) from a light measurement (lamp was fired). Averages of fifteen measurements were taken for each spectrum. Reflectance values were calculated by dividing each spectrum by the spectrum obtained with the calibration medium. The integration time of the spectrometer was the same for the measurements taken by both the tissue media and the calibration media, and it was varied between 8 and 60 ms such that the signal to noise ratio was at least 25:1.

The measurements were taken by inserting the fiber probe into the liquid media. The diameter of the fiber probe housing was large enough (3 mm) compared to the fiber separation (250 μm), such that there was no difference between measurements taken at the surface of the media or submerging the probe inside the sample. The end of the fiber probe was located more than 1 cm from the bottom and walls of the container to avoid interference from the boundaries.

Example 1b

Development of an Analytical Model as Described Herein

A. Reflectance as a Function of the Reduced Scattering Coefficient

For the development of the model described herein, the reflectance from a medium that scatters light was analyzed for conditions with very little absorption ($\mu_a^1 \leq 0.01$ cm$^{-1}$). MC simulations were run for a medium with an absorption coefficient of 0.01 cm$^{-1}$ and for five values of reduced scattering coefficient ($\mu_s'$=5, 10, 15, 20 and 25 cm$^{-1}$). The anisotropy value was set to 0.9. Four different fiber tilt angles were modeled (θ=0, 15, 30 and 45 degrees). The absolute reflectance ($R^{ABS}$), is defined as the ratio of the collected light (I) over the incident light ($I_0$), and is calculated using Eq. (1):

$$R^{ABS} = \frac{I}{I_0} = \frac{\sum_{i=1}^{TPC} \exp(-\mu_a l_i)}{TPL} \tag{1}$$

where TPC is the Total number of Photons Collected, TPL is the Total number of Photons Launched, $\mu_a$ is the absorption coefficient and $l_i$ is the path-length of each collected photon. To analyze the reflectance experimentally, eight tissue media were prepared with different concentrations of Intralipid-10% in deionized water. No dye was added; therefore the absorption coefficient was assumed to be negligible for the spectral range studied. The resulting reduced scattering coefficients of the tissue media varied between 3 and 20 cm$^{-1}$. Measurements were taken on each media with each of the four fiber optic probe configurations. It is difficult to determine experimentally the absolute value of the incident light; however, a relative value of the incident light can be obtained by measuring the collected light from a calibration medium. The relative reflectance of a medium ($R_P^{REL}(\lambda)$) has been defined as the ratio of the absolute reflectance of a medium ($R_P^{ABS}(\lambda)$) over the absolute reflectance of a calibration medium ($R_C^{ABS}(\lambda_0)$). As described herein, $R_C^{ABS}(\lambda_0)$ represents absolute reflectance of the calibration medium at $\lambda_0$=610 nm, which will be a constant given that the same calibration medium and wavelength is always used. If the incident light of the reflectance measurements in the tissue and calibration medium is the same ($I_0(\lambda)=I_0(\lambda_0)$), the expression for the relative reflectance will be independent of the incident light, as described in Eqn. 2.

$$R_P^{REL}(\lambda) = \frac{R_P^{ABS}(\lambda)}{R_C^{ABS}(\lambda_0)} = \frac{I_P(\lambda)}{I_0(\lambda)} \frac{I_0(\lambda_0)}{I_C(\lambda_0)} = \frac{I_P(\lambda)}{I_C(\lambda_0)} \tag{2}$$

where $I_P(\lambda)$ is the collected light from the tissue medium and $I_C(\lambda_0)$ is the collected light from the calibration medium at 610 nm. Note that since $R_C^{ABS}(\lambda_0)$ is a constant, $R_P^{REL}(\lambda)$ is linearly proportional to $R_P^{ABS}(\lambda)$. A simplified variation of Eqn 2. is described herein as "Equation (1)" in the Summary Section and the Claims section, as shown as:

$$R = \frac{S_P(\lambda)}{S_C(\lambda)} R_C(\lambda) \qquad \text{Equation (1)}$$

Figure 4:
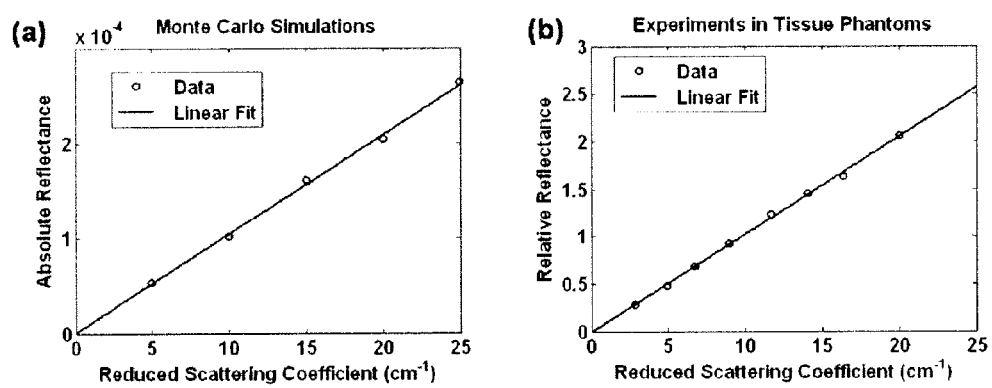
FIG. 4 Reflectance as a function of reduced scattering coefficient for a 45 degree fiber probe configuration in a non-absorbing medium obtained with (a) Monte Carlo simulations and (b) experiments in tissue media.

The relative reflectance of the tissue media were calculated, at the wavelength of 610 nm, as the ratio of the tissue medium measurement over the measurement obtained with the calibration medium. The incident light on the tissue and calibration media was the same. Reflectance as a function of reduced scattering coefficient, using a 45 degree fiber probe configuration, obtained with MC simulations and experiments in tissue media is shown in FIGS. 4a and 4b, respectively. It is observed that there is a linear relationship between reduced scattering coefficient and reflectance. Equation 3 is a straight-line fit to the data using linear least squares, where R(0) is reflectance when there is negligible absorption.

$$R(0) = a\mu_s' + a_0 \tag{3}$$

Similar results were obtained with 0, 15 and 30 degree fiber probe configurations (data not shown).

The determined values of coefficients a and $a_0$ are presented in Table 1. The reason that the values obtained with MC simulations and experiments in tissue media differ is because MC simulations determine absolute reflectance values, and the experiments determine relative reflectance values (i.e., the precise amount of light emitted by the source fiber was not measured). The value of $a_0$ is a function of the anisotropy value and phase function of the scattering centers, as it will be discussed in Section C.

B. Reflectance as a Function of the Reduced Scattering and Absorption Coefficient To further develop the model described herein, reflectance was analyzed for conditions where the tissue medium both scatters and absorbs light. MC simulations were run for a medium with nineteen values of absorption coefficient ($\mu_a$=0.1 to 10 cm$^{-1}$) and for three values of reduced scattering coefficient ($\mu_s'$=5, 10 and 20 cm$^{-1}$). The anisotropy value was set to 0.9. Four different tilt angles were modeled (θ=0, 15, 30 and 45 degrees). The absolute reflectance was calculated using Eq. (1).

For the experiments, liquid tissue media were prepared with three values of reduced scattering coefficient ($\mu_s'$=5.5, 10.6 and 20.7 cm$^{-1}$) and nineteen values of absorption coefficient ($\mu_s'$=0.12 to 8 cm$^{-1}$). The values of the optical properties, quoted at 610 nm, were selected based on a range of values commonly found in tissue[39]. Measurements were taken on each medium with each of the four fiber optic probe configurations. The relative reflectance was calculated at the wavelength of 610 nm by dividing the tissue medium measurements by the measurements obtained with the calibration medium.

Reflectance as a function of absorption coefficient for several reduced scattering coefficient values, using a 45 degree fiber probe configuration, obtained with MC simulations and experiments in tissue media is presented in FIGS. 5a and 5b, respectively. Similar results were obtained with the 0, 15 and 30 degree fiber probe configurations (data not shown).

From the previous section, it was determined that reflectance is linearly proportional to reduced scattering coefficient when there is negligible absorption. Beer's law, states that the intensity should decay exponentially as a function of absorption coefficient; therefore, the model is expanded using Eq. (4):

$$R(\mu_a) = R(0)\exp(-\mu_a \langle L \rangle) \quad (4)$$

where R(0) is given by Eq. 3, and $\langle L \rangle$ is the "mean average path-length" of the collected photons, as defined in Ref. 40.

The mean average path-length of the collected photons can be described as being inversely proportional to both the scattering and absorption properties of a medium, for small source-detector separations. For that geometry, the collected photons from a highly-scattering medium reverse their direction close to the surface of the tissue and travel a short path.

Conversely the photons collected from a low-scattering medium penetrate a longer distance into the medium before scattering and reversing their directions. The mean average path-length of the collected photons is also longer in a low-absorption medium than in a high absorbing medium because the probability for a collected photon to travel a long path is reduced for the latter case. The model for the mean average path-length is given by Eq. (5):

$$\langle L \rangle = \frac{b}{(\mu_a \mu_s')^c} \quad (5)$$

where b and c are fitting coefficients. Equation 6 is obtained by combining Eqs. (3), (4) and (5).

$$R(\mu_a) = (a\mu_s' + a_0)\exp\left(-\mu_a \frac{b}{(\mu_a \mu_s')^c}\right) \quad (6)$$

Figure 5:
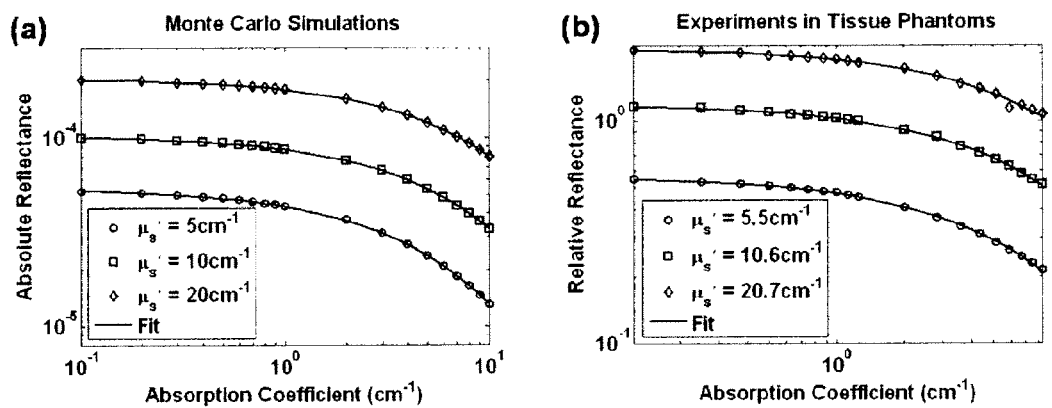
FIG. 5 Reflectance as a function of absorption coefficient for a 45 degree fiber probe configuration obtained with (a) Monte Carlo simulations and (b) experiments in tissue media.

Equation 6 was used to provide the fit to the reflectance measurements shown in FIG. 5, for which a, $a_0$, $\mu_a$ and $\mu_s'$ were known, and the values of b and c were determined (Table 2 and Table 3). A simplified variation of Eqn. 6 is described herein as "Equation (2)" in the Summary and Claims section and is shown as:

$$R = (a\mu_s')\exp\left(-\mu_a \frac{b}{(\mu_a \mu_s')^c}\right) \quad \text{Equation (2)}$$

It is noted that for a given tilt-angle fiber probe, the values of b and c agree well for the three different reduced scattering coefficients, which validates the model described herein. The values of b differ between MC simulations and experiments, while the values of c agree well.

The MC simulations were repeated with the same conditions described in Sections A and B but the indices of refraction of the fiber ($n_f$) and medium ($n_m$) were set to 1.46 and 1.33, respectively. The simulations were run only for a 0 and 45 degree fiber probe. The value of the coefficients a and $a_0$ and the mean value of the coefficients b and c are listed in Table 4 under column "B". The values of the coefficients obtained with MC simulations in Tables 1, 2 and 3 are listed in Table 4 under column "A". As a result, the values of the coefficients do not depend on indices of refraction of a fiber and a medium.

The MC simulations were analyzed with the same conditions described in Sections A and B but with the center-to-center fiber separation set to 200 μm. The simulations were only run for a 0 and 45 degree fiber probe configuration. The values of the coefficients a, $a_0$ and the mean value of the coefficients b and c are listed in Table 4 under column "C". The values of a and b depend on the center-to-center separation of the fibers.

Finally, the same experimental data described in Sections A and B were re-analyzed with a tissue medium prepared with deionized water and Intralipid. The values of a obtained for the 0, 15, 30 and 45 degree fibers were 0.19, 0.18, 0.18 and 0.18, respectively, and the values for $a_0$ were −0.06, −0.06, −0.05 and −0.02, respectively. The values of the coefficients b and c were the same as the values listed in Tables 2 and 3, indicating that the calibration medium only affects the coefficients a and $a_0$ in a linear manner. The fact that only coefficients a and $a_0$ are dependent on the calibration medium is reasonable, because a change in calibration medium is reflected in the value of $R_C^{ABS}(\lambda_0)$; therefore, there is only a linear change in $R_P^{REL}(\lambda)$, as defined by Eqn. 2.

C. Reflectance as a Function of the Anisotropy Value and the Phase Function

At small source-detector separations, where the diffusion approximation does not apply, the reflectance of light is a function of absorption coefficient, scattering coefficient, phase function of the scattering centers, boundary conditions and properties of the source and collection fibers. Phase functions have typically been modeled using either Mie Theory[41], the Henyey-Greenstein approximation[34] or the modified Henyey-Greenstein approximation[9,35]. It has been previously reported that the choice of phase function can have a significant effect on the reflectance of light for small source-detector separations[42,43]. When using a mono disperse suspension of spherical particles, the Mie scattering presents very distinguishable oscillations, but as the size distribution increases, the Mie oscillations smooth out[44], and the signal is also masked by a background of diffusely scattered light from the underlying tissue[45].

To determine the influence of anisotropy value on reflectance measurements, the Henyey-Greenstein approximation was chosen, because it has been commonly used to model the phase function of scattering centers at small source-detector separations[7,8,11,12,14,16,19,21,46,47]. MC simulations were run for a medium with an absorption coefficient of 0.01 cm$^{-1}$ and for a fiber probe tilt angle of 0 and 45 degrees. Fifteen simulations were performed, for each tilt angle, using five different anisotropy values (g=0.2, 0.5, 0.75, 0.9 and 0.95), and three different reduced scattering coefficient values ($\mu_s'$=5, and 20 cm$^{-1}$). Absolute reflectance was determined using Eq. (1). For each reduced scattering coefficient, the percentage variation (PV) of the reflectance referenced to the reflectance with g=0.9 was calculated using Eq. (7), where R1 is the reflectance at a given g value and R2 is the reflectance at g=0.9.

$$PV = \frac{(R1 - R2)}{R2} \times 100 \quad (7)$$

Figure 6:
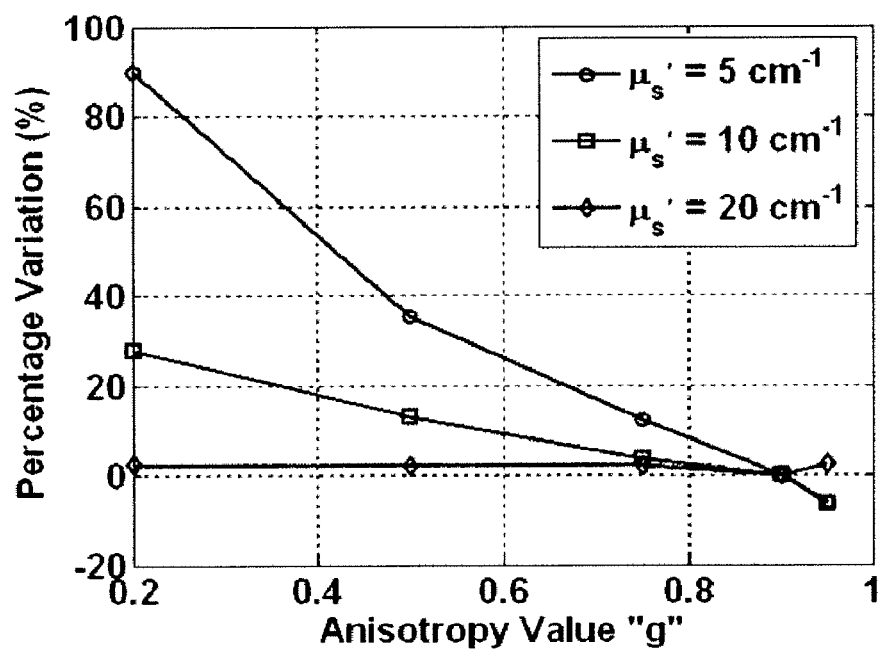
FIG. 6 Percentage variation of reflectance as a function of anisotropy value for the 0 degree fiber probe configuration obtained with Monte Carlo simulations.

The percentage variation, for a 0 degree fiber tilt angle, as a function of anisotropy value for different reduced scattering coefficients is depicted in FIG. 6. Higher reduced scattering coefficient values exhibit lower percentage variation as a function of the g value, compared to lower reduced scattering coefficient values. The percentage variation for all values of f $\mu_s'$ is less than 15% for typical biological tissue anisotropy values (g>0.75). Similar results were obtained with a 45 degree tilt angle.

The MC simulations described in Sections A and B were repeated to calculate values of the coefficients a, $a_0$ and mean values of the coefficients b and c with a 0 and 45 degree fiber probe configuration for the anisotropy values of 0.2, 0.5, 0.75 and 0.95. Results for the anisotropy values of 0.2, 0.5, 0.75 and 0.95 are listed in Table 4 under columns "E", "F", "G" and "H", respectively. Values of $a_0$ and b vary significantly from the results in column "A" for low g values, and do not depend on anisotropy value for high g values. For biological tissues high anisotropy values are the most applicable.

Figure 7:
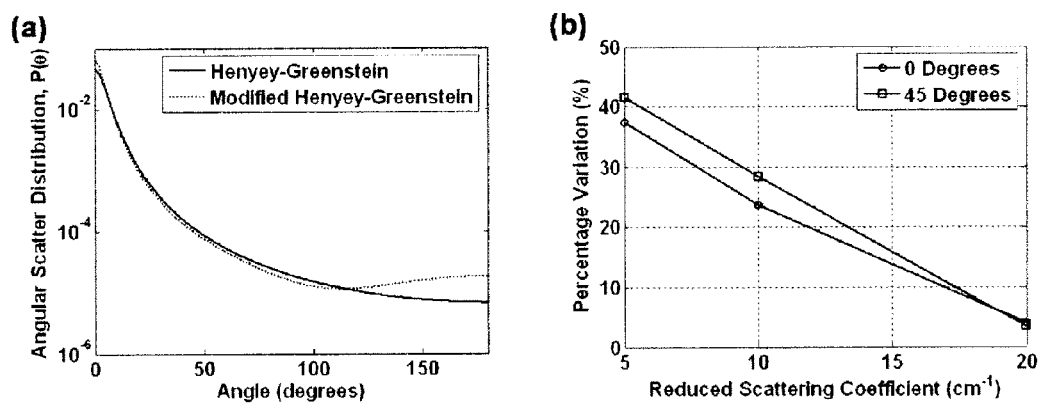
FIG. 7 (a) Angular scatter distribution of HG and MHG phase function. (b) Percentage variation of reflectance between HG and MHG phase function as a function of the reduced scattering coefficient for a 0 and 45 degree fiber probe configuration obtained with Monte Carlo simulations.

To analyze the influence of the phase function on our model, the Monte Carlo code was altered to model a modified Henyey-Greenstein phase function[9,35]. The angular scatter distribution of the MHG ($p_{MHG}$) is described by Equation (8).

$$p_{MHG}(\theta, g_{HG}, \xi) = \xi p_{HG}(\theta, g_{HG}) + (1-\xi)\frac{3}{4\pi}\cos^2\theta \quad (8)$$

where $g_{HG}$ and $p_{HG}$ are the anisotropy value and the angular scatter distribution of the HG phase function, respectively, and $\xi$ is a normalization factor. The value of $g_{HG}$ was set to 0.9165 and $\xi$ was set to 0.9, such that the anisotropy value of the MHG was 0.9. FIG. 7a plots the angular scatter distribution of the HG and MHG phase functions where both anisotropy values are equal to 0.9.

Monte Carlo simulations with HG and MHG phase function were performed, for a 0 and 45 degree fiber probe, with a $\mu_s'$=5, 10 and 20 cm$^{-1}$, g=0.9 and $\mu_a$=0.01 cm$^{-1}$. FIG. 7b shows a percentage variation between reflectance obtained with HG and MHG phase functions, given by Equation 7 where R1 is reflectance obtained with the MHG phase function and R2 is reflectance obtained with the HG phase function at a given $\mu_s'$. It is observed that higher $\mu_s'$ values present smaller percentage variation between the two phase functions.

The Monte Carlo simulations described in Sections A and B were repeated with the MHG phase function for the 0 and 45 degree fiber probe. The values of the coefficients a, $a_0$ and the mean value of the coefficients b and c are listed in Table 4 under column "D". Only $a_0$ appears to vary significantly from the results presented in column "A".

D. Extraction of the Optical Properties of a Tissue from Monte Carlo Simulations To validate the model described by Eq. (6), the optical properties of a scattering and absorbing medium were extracted from reflectance obtained from MC simulations (Section D) and from experiments in tissue media (Section E).

The value of $a_0$ is dependent on both phase function and anisotropy value, as described in Section C. The phase function and anisotropy value of the scattering centers are wavelength dependent, and are typically unknown in biological tissue; therefore, to simplify the use of the model described in Equation 6, the value of $a_0$ was set to 0.

Two absolute reflectance spectra were generated with MC simulations using a 45-degree fiber probe. Both spectra have the same reduced scattering coefficient, but different absorption coefficient values, which will be referred to as Low$\mu_a$ and High$\mu_a$ spectra. Wavelengths were selected for the range between 500-750 nm in 10 nm steps. The reduced scattering coefficient was modeled using Eq. (9):

$$\mu_s'(\lambda) = d\lambda^{-e} \quad (9)$$

The value of the exponent e was set to 1.1, based on typical values found in biological tissue[48], and the value of d was selected such that $\mu_s'(610\,\text{nm})=10\,\text{cm}^{-1}$. The anisotropy value was held constant at 0.9 for all wavelengths. The absorption coefficient was represented by Eq. (10):

$$\mu_a(\lambda) = f_1(f_2\epsilon_{HbO}(\lambda) + (1-f_2)\epsilon_{Hb}(\lambda)) \quad (10)$$

where $\epsilon_{HbO}(\lambda)$ and $\epsilon_{Hb}(\lambda)$ are the extinction coefficients of oxyhemoglobin and deoxyhemoglobin, respectively. The values of $f_1$ were selected such that $\mu_a(610\,\text{nm})=0.2\,\text{cm}^{-1}$ for the Low$\mu_a$ spectrum, and $\mu_a(610\,\text{nm})=1\,\text{cm}^{-1}$ for the High$\mu_a$ spectrum. The value of $f_2$, which represents oxygen saturation, was set to 0.8.

To extract optical properties from an MC simulation, Eq. (6) was fitted to the absolute reflectance spectrum, for which the values of a, b and c were obtained from Tables 1, 2 and 3, respectively; d, e, $f_1$ and $f_2$ were the fitting parameters, and $a_0$ was set to 0. The parameters were bounded as $0 \leq d$, e, $f_1$ and $0 \leq f_2 \leq 1$.

Figure 8:
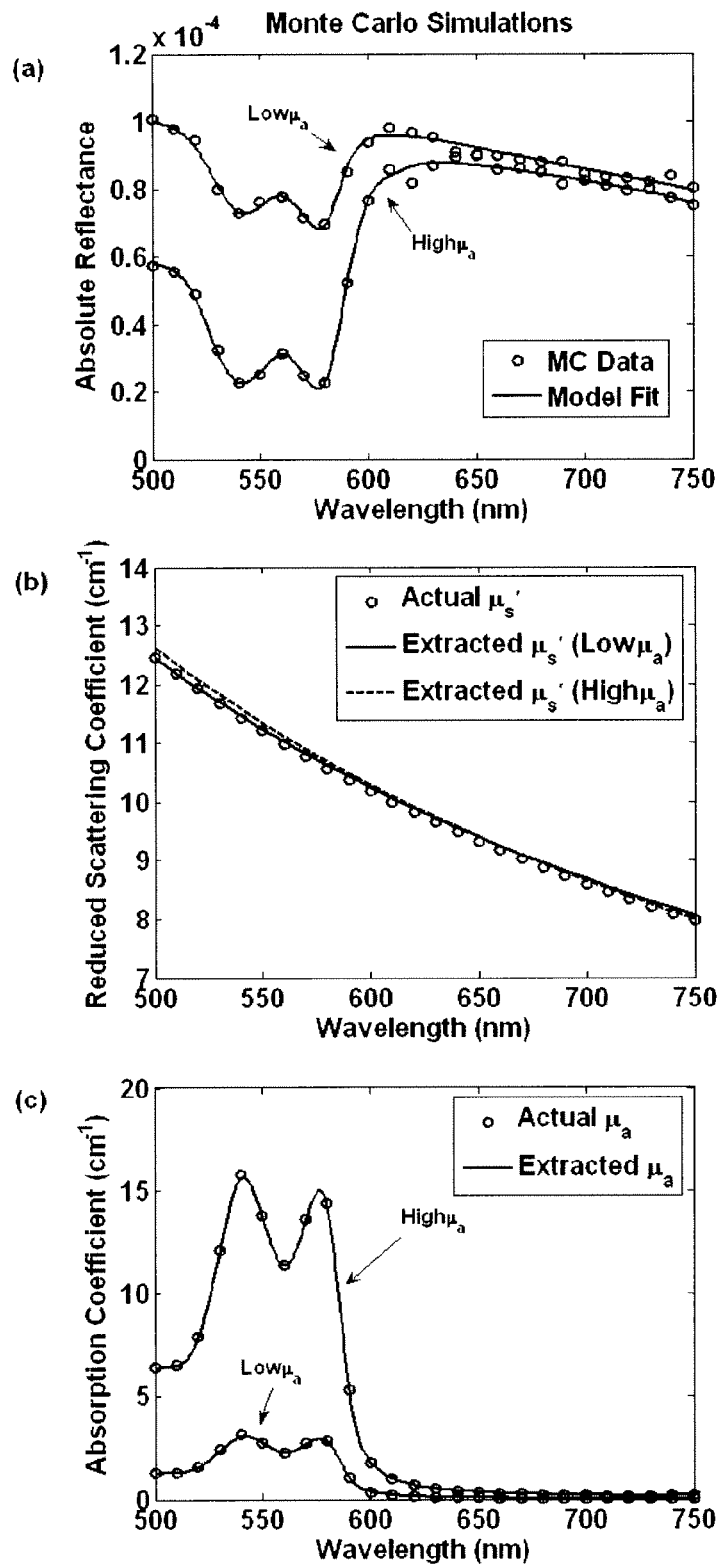
FIG. 8 (a) Absolute reflectance spectrum and a model fit for a Monte Carlo simulation with a 45 degree fiber probe configuration. Actual and extracted (b) reduced scattering coefficient and (c) absorption coefficient.

FIG. 8a shows the absolute reflectance spectrum and the least square fit to the model, for the Low$\mu_a$ and High$\mu_a$ spectra. Actual and extracted wavelength-dependent reduced scattering coefficients are shown in FIG. 8b, and the actual and extracted wavelength-dependent absorption coefficients are shown in FIG. 8c. The values of hemoglobin oxygen saturation ($f_2$) obtained were 0.826 and 0.836 for the Low$\mu_a$ and High$\mu_a$, respectively.

E. Extraction of the Optical Properties of a Tissue Medium

Eight liquid tissue media were prepared with different optical properties. Two reduced scattering coefficients were used, such that $\mu_s'(610\,\text{nm})$ was 9.2 and 17.5 cm$^{-1}$, and four absorption coefficients were used such that $\mu_a(610\,\text{nm})$ was 0, 0.5, 2.8 and 8.5 cm$^{-1}$. Measurements were taken with four fiber probe configurations.

Using Eq. 3, values of a obtained in Table 1 and the determined values of reduced scattering coefficient of the calibration medium ($\mu_s'c$), it was possible to determine theoretically the relative reflectance of the calibration medium ($R_C^{REL}(\lambda) = R_C^{ABS}(\lambda)/R_C^{ABS}(\lambda_0) = \alpha\mu_{sC}'(\lambda) + a_0$) when the absorption coefficient is negligible. Because the wavelength-dependent phase function and anisotropy value of the calibration medium are not known, the model can be simplified by setting the value of $a_0$ to 0. The incident light at a given wavelength is not necessarily equal to $I_0(\lambda_0)$; therefore, the relative reflectance of the tissue medium as a function of wavelength ($R_P^{REL}(\lambda)$), can be calculated with Eq. (11).

$$\begin{aligned}R_P^{REL}(\lambda) &= \frac{R_P^{ABS}(\lambda)}{R_C^{ABS}(\lambda_0)} \\ &= \frac{R_P^{ABS}(\lambda)}{R_C^{ABS}(\lambda_0)}\frac{R_C^{ABS}(\lambda)}{R_C^{ABS}(\lambda_0)}\frac{R_C^{ABS}(\lambda)}{R_C^{ABS}(\lambda_0)} \\ &= \frac{R_P^{ABS}(\lambda)}{R_C^{ABS}(\lambda)}R_C^{REL}(\lambda) \\ &= \frac{I_P(\lambda)I_0(\lambda)}{I_0(\lambda)I_C(\lambda)}a\mu_{sC}'(\lambda) \\ &= \frac{I_P(\lambda)}{I_C(\lambda)}a\mu_{sC}'(\lambda)\end{aligned} \quad (11)$$

where $I_P(\lambda)$ is the collected light obtained from the tissue medium and $I_C(\lambda)$ is the collected light obtained from the calibration medium.

Figure 9:
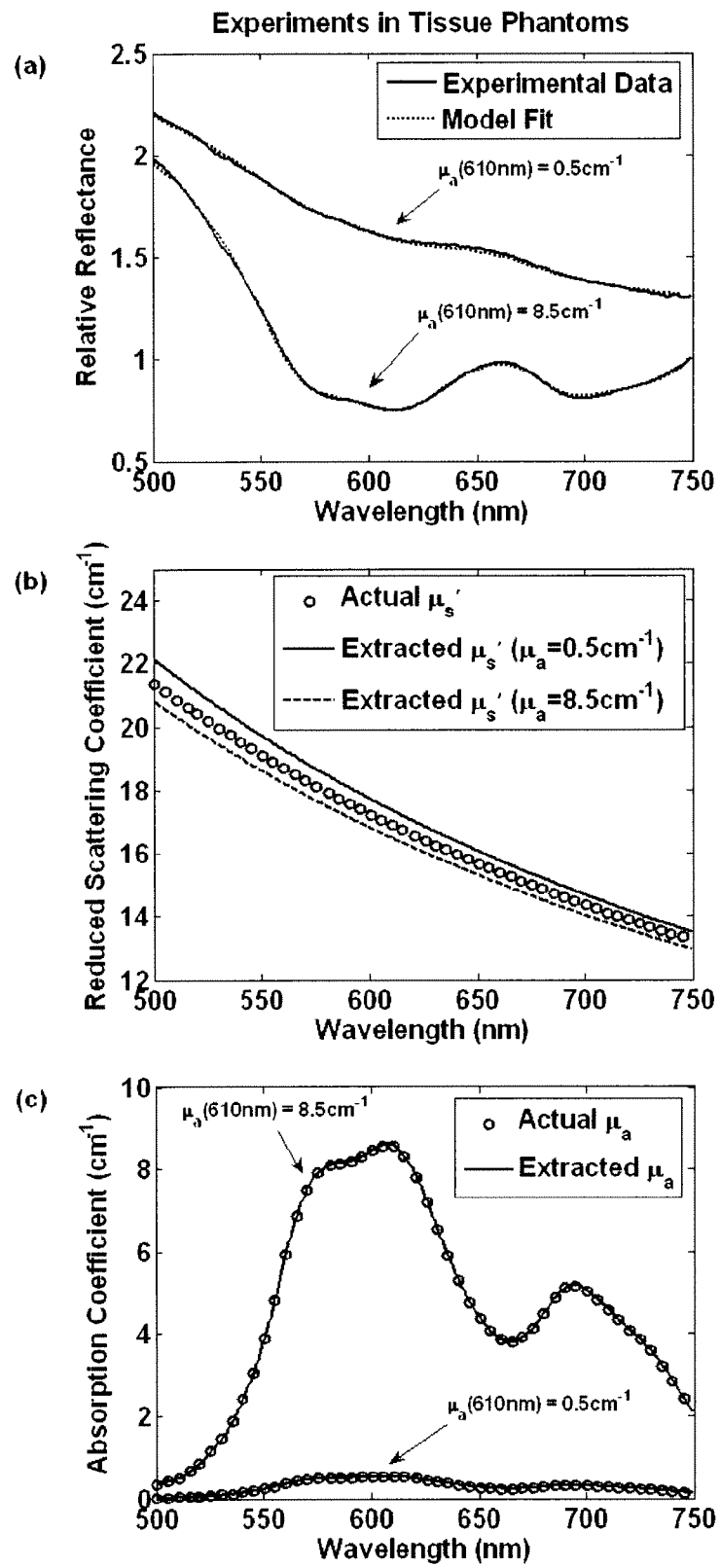
FIG. 9 (a) Relative reflectance spectrum and a model fit for experiments in a tissue calibrating medium with a 45 degree fiber probe configuration. Actual and extracted (b) reduced scattering coefficient and (c) absorption coefficient.

Eq. (6) was then fitted to $R_p^{REL}(\lambda)$ for the wavelengths of 500-750 nm. The reduced scattering coefficient was modeled by Eq. (9) and the absorption coefficient was modeled with Eq. (12):

$$\mu_a(\lambda) = f_1 \epsilon_{Dye}(\lambda) \quad (12)$$

where $\epsilon_{Dye}(\lambda)$ is the extinction coefficient of the Indigo Blue dye. The fitting coefficients were bounded by $0 \leq d, e, f_1$, the values of a, b and c were obtained from Tables 1, 2 and 3, respectively, and $a_0$ was set to 0. FIG. 9a shows the relative reflectance spectrum and the least square fit to the model, using a 45 degree fiber optic probe configuration, for $\mu_s'(610 \text{ nm})=17.5 \text{ cm}^{-1}$ and $\mu_a(610 \text{ nm})=0.5$ and $8.5 \text{ cm}^{-1}$. Actual and extracted wavelength-dependent reduced scattering coefficients are shown in FIG. 9b, and the actual and extracted wavelength-dependent absorption coefficients are shown in FIG. 9c.

Tables 5 and 6 depict mean and standard deviation values of absorption and reduced scattering coefficients over fifteen measurements determined with all the fiber probe configurations in the eight media at 610 nm, respectively. The errors in estimating the absorption and scattering coefficients between mean $\mu_a$ and "Actual $\mu_a$" was less than 20% and between the mean $\mu_s'$ and "Actual $\mu_s'$" was less than 10%.

Analysis was also performed by using a tissue medium prepared with Intralipid and deionized water, which has different optical properties than that of a titanium dioxide suspension. The errors in estimating $\mu_a$ and $\mu_s'$ were slightly reduced; however, the disadvantage of using Intralipid as a calibration medium is that its optical properties can change with time as the solution degrades.

An analytical model for describing the reflectance of a scattering and absorbing medium is described herein. The model is successful in describing the reflectance spectrum at small source-detector separations and is not limited to a parameter range with scattering much larger than absorption, a limitation that generally plagues models based on diffusion theory.

Monte Carlo simulations indicate that tilting both source and detector optical fibers, such that the fibers are parallel in respect to each other, enhances the sensitivity to superficial volumes of tissue, while maintaining a fiber-probe geometry that is convenient for clinical applications and is easy to fabricate. The model has been shown herein for fiber probe tilt angles between 0 and 45 degrees.

The model is defined by Eq. (6), (and Equation (2) as depicted in the Summary and Claims section) and the coefficients a, $a_0$, b and c are listed in Tables 1, 2 and 3. The value of the coefficient a differs between the MC simulations and the experiments in tissue media because the former measures absolute reflectance while the latter measures relative reflectance. The values of a and $a_0$ depend on optical properties of the calibration medium. If a calibration medium with different optical properties is used, new values for a and $a_0$ should be determined experimentally as described in Section A. A change in the optical properties of a calibration medium is reflected in the value $Rc^{ABS}(\lambda_0)$, which translates to a linear change of $R_p^{REL}(\lambda)$, as defined by Equation 2. Therefore, only values of a and $a_0$ are affected by the details of the calibration medium, while the values of b and c remain the same, as it was demonstrated by comparing the results of using a calibration medium made with Intralipid instead of titanium dioxide. Although any wavelength of the calibration medium could be used as a reference herein, the value of 610 nm was chosen, because it matches the absorption peak of the Indigo Blue dye.

Typically, reflectance measurements are calibrated by dividing the tissue spectral measurement by a spectrum measured with a spectrally-flat diffuse-reflector reference material instead of a calibration medium measurement as described in this paper. Advantages of using an immersion-type liquid calibration medium as a reference, as described herein, are:

1) When using a diffuse reflector, the distance between the fiber probe and the reflector surface must be fixed and repeatable if absolute values for optical properties are sought, as opposed to submerging the fiber probe in the liquid calibration medium, which minimizes the possibility of error and is easily repeatable.
2) A fiber probe with tips faceted at 45 degrees exhibits total internal reflection when the fiber tip is in air; however, most of the light emerges when the fiber tip is in contact with water (or tissue).

The model for the mean average path-length expressed by Eq. (5) was determined intuitively and verified empirically. Although an analytical derivation for the mean average path-length is not provided, it has been shown herein that Eq. (5) enables successful modeling of the reflectance spectrum of a turbid medium with good accuracy, when it is incorporated in the model defined by Eq. (6).

For a given tilt-angle fiber probe, values of the coefficients b and c agree well for different values of $\mu_a$ and $\mu_s'$, which validates the model described herein, as observed in Tables 2 and 3. The value of c is determined to be between 0.19-0.21 by both MC simulations and experimental results; however, there is disagreement for the value of b. Although the source of the discrepancy has not been determined, it is noted that it is consistent with the fact that the center-to-center fiber separation of the fiber probes fabricated were approximately 238 µm, instead of 250 µm as was used in the simulations. Table 4 indicates that the value of b depends on the fiber separation, as observed when comparing b values obtained with probes that have a separation of 200 µm and 250 µm. The value of b increases for smaller anisotropy values but the experimental tissue media are highly forward scattering; therefore, variation of b is not attributed to the small anisotropy values.

Based on MC simulations and the results presented in Table 4, the coefficients of the model can be determined, which do not depend on the indices of refraction of the fiber and the medium, and if the same phase function is used, the coefficients are not affected for different values of highly forward scattering anisotropies. However, the coefficient $a_0$ is affected by the phase function and by low anisotropy values.

At small source-detector separations, the reflectance spectrum is dependent on the details of the phase function and the anisotropy value of the scattering centers. The reflectance was calculated for different anisotropy values using the Henyey-Greenstein approximation and was also calculated using MHG phase functions with an anisotropy value of 0.9. It was determined that reflectance is sensitive to anisotropy value and phase function for low scattering coefficients, but relatively insensitive for high scattering coefficients, where the photons undergo more scattering events before being collected, which allows the photons to lose track of their original directions. This effect can be observed in FIGS. 6 and 7b. It was also determined that for anisotropy values typically found in tissue (g>0.75), the reflectance varies less than 15% for all values of $\mu_s'$.

The model was tested by reconstructing the optical properties of a spectral reflectance obtained from MC simulations. The extracted values for reduced scattering and absorption coefficients agree well with actual values (FIGS. 8b and 8c). The values of hemoglobin oxygen saturation extracted were also close to the actual values. This validates the inversion algorithm with an approach that can be used in vivo in biological tissue with typical values of optical properties.

The model described herein was tested in tissue media, and the values of the extracted optical properties agree well with the actual values (Tables 5 and 6) of the prepared media. The errors for the absorption coefficient were less than 20%, while the errors for the reduced scattering coefficient were less than 10%. Equation 11 depends on $R_C^{REL}(\lambda)$, which is calculated theoretically by setting $a_0=0$. The data was reanalyzed by using a tissue medium made from Intralipid, for which the results were slightly improved, indicating that the real values of $a_0$ in Intralipid, for all wavelengths, are closer to 0 than is the case for a suspension of titanium dioxide. The disadvantage of using Intralipid as a tissue calibrating medium is that its optical properties are less stable over time.

The phase function and anisotropy value of real tissue is not well defined and is wavelength dependent; therefore, the specific value of $a_0$ is unknown. By setting $a_0$ to 0 the effect of the phase function of the scattering centers is assumed to be small throughout the model; hence, the model described herein is a simplification of light transport in a turbid medium. A study described herein in Example 2 assess the validity of the model described herein for a wide range of phase functions and anisotropy values found in biological tissues. The reduced scattering and absorption coefficients were reconstructed with good accuracy by applying an analytical model described herein.

The model is applicable for fiber probe configurations with various tilt angles, for the geometry depicted in this paper. Fiber probes with this geometry are compatible with endoscope channels, which will allow measurements in tissues such as the colon and esophagus. The model has been empirically derived and validated using both MC simulations and experiments in tissue media.

Example 2

An Exemplary Model for Extracting Absolute Optical Properties of a Biological Tissue Non-invasive optical reflectance measurements have been used to extract diagnostic information from a variety of tissue types, in vivo, such as colon[49], skin[50], brain[51], cervix[52], esophagus[53], prostate[54] and bronchial mucosa[55]. The typical experimental setup of these systems often consists of a fiber probe with a diameter of a few millimeters or less, with one or more fibers that transmit light to and from the tissue. An earlier ex vivo study reported that the amount of pressure applied on a sample of tissue affects its absorption and reduced scattering coefficients[56]. It has also been reported that probe pressures with forces of less than 1 Newton do not affect the fluorescence intensity or lineshape of measurements obtained in vivo on cervical tissues[57].

Described herein is a model of the influence of probe pressure on spectral reflectance measurements of biological tissue in vivo. The thigh muscle of a mouse was used as a tissue model because the volume of the tissue is large enough to be considered semi-infinite for the optical geometry of a probe (source-detector separation of approximately 250 μm), and because the muscle is relatively homogeneous.

Figure 10:
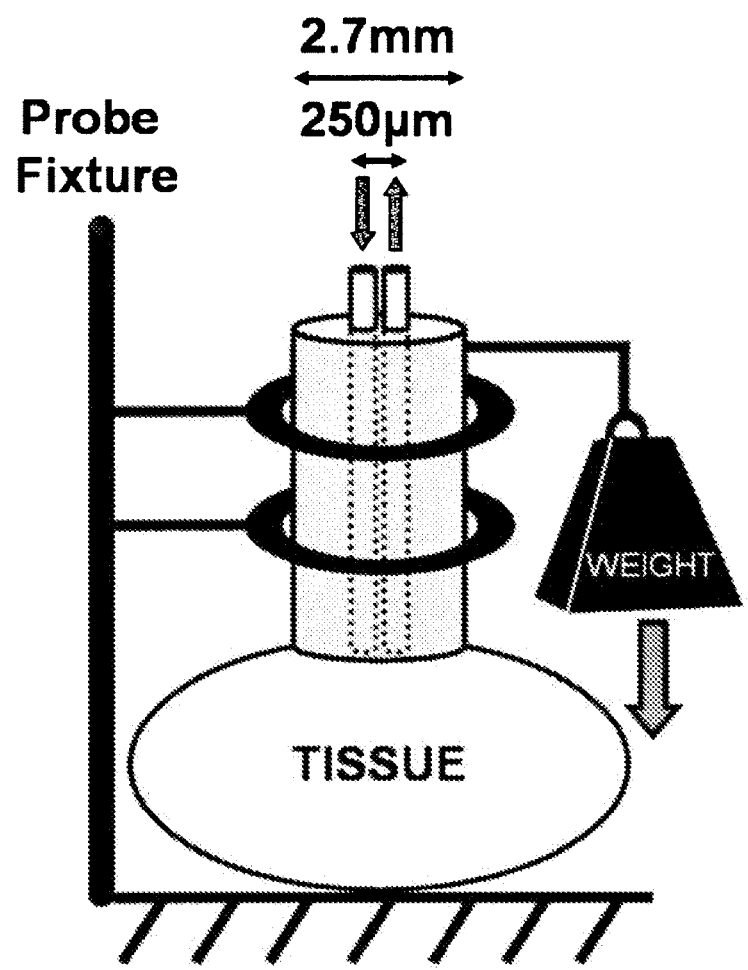
FIG. 10 Schematic diagram of an experimental set-up for extracting optical properties from a biological tissue.
Figure 11:
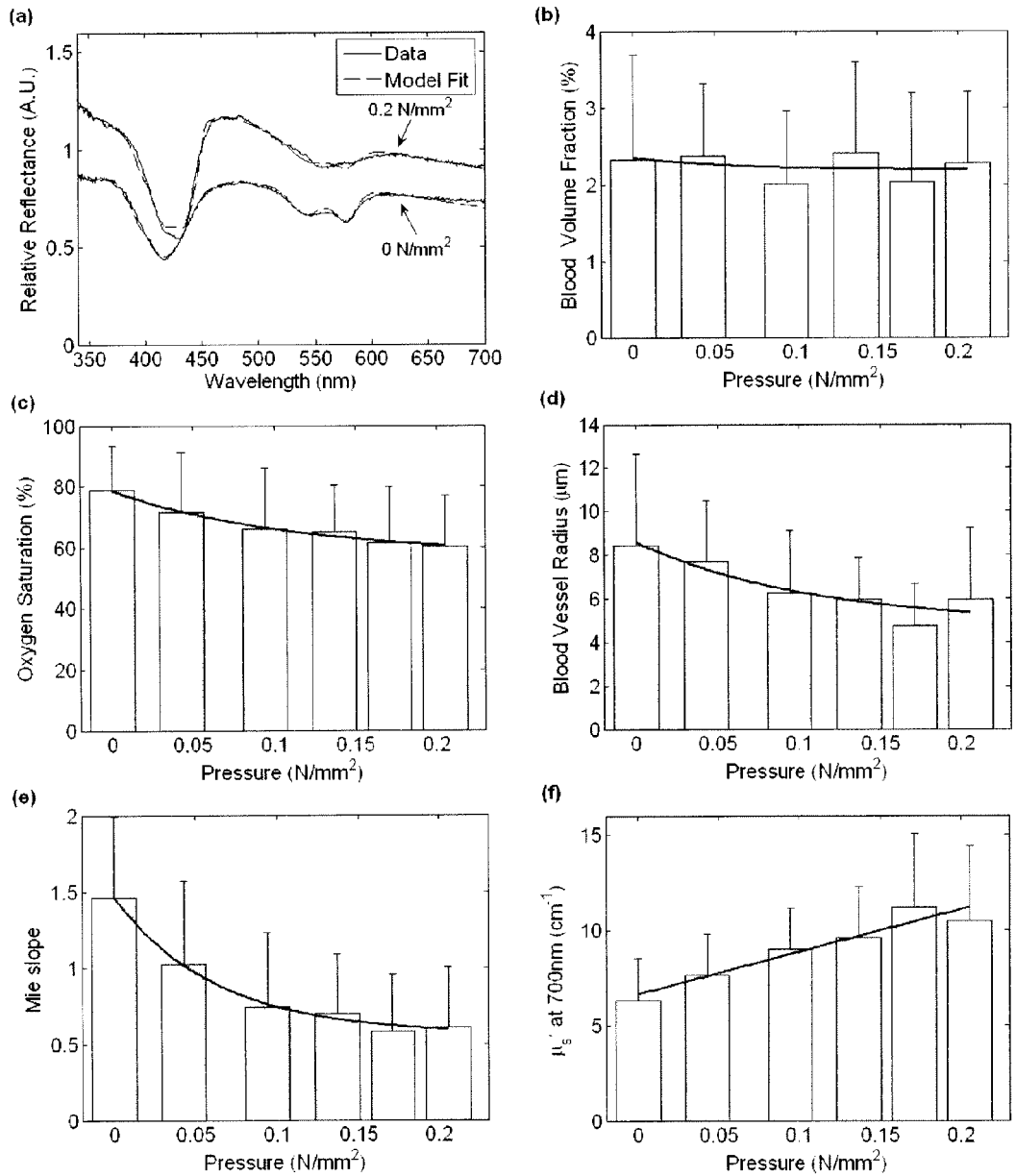
FIG. 11 (a) An example of relative reflectance and respective fits for a measurement obtained with a pressure of 0 and 0.2 N/mm$^2$. Mean and standard deviations of (b) blood volume fraction, (c) oxygen saturation, (d) mean blood vessel radius, (e) Mie slope and (f) reduced scattering coefficient at 700 nm as a function of the probe pressure. The solid line is the least-squared fit of Eqn. 5 to the mean values of each parameter.

The experimental set-up comprises a pulsed Xenon arc lamp (Perkin Elmer, LS1130-3) as a light source, a spectrometer with a linear CCD array detector (Ocean Optics, S2000), a control computer, and a fiber optic probe, which transmits light to and from the tissue. The fiber probe contains two optical fibers with core diameters of 200 μm, a numerical aperture of 0.22 and a center-to-center separation of approximately 250 μm. The optical fibers are encapsulated within a metal-tube that has a diameter of 2.7 mm. The probe has a handle where different weights can be attached, as shown in FIG. 10. The weights, added to the weight of the probe itself, resulted in applied forces of 0.24, 0.53, 0.78, 0.98 and 1.17 Newtons over a probe area of 5.72 mm$^{50}$, which correspond to pressures of 0.04, 0.09, 0.13, 0.17 and 0.2 N/mm$^{50}$.

Ten mice were anesthetized with pentobarbital, and the skin over both the left and right thigh muscles was removed, such that the muscles were exposed. The probe was placed perpendicular to the tissue surface, on the muscle, for the optical measurements. A measurement consisted of an average of five spectra, each spanning the wavelength range of 340 to 700 nm. Optical contact between a fiber probe and the tissue was assisted by applying water to the surface of the muscle.

The experiment was performed on the thigh muscle of each leg. The data could not be collected from one muscle; therefore, experimental data from 19 thigh muscles (9 left and 10 right) are described herein. Each experiment comprised five sets, and a set consisted of two measurements. The first measurement was obtained when the fiber probe was placed in gentle contact with the surface of the tissue such that there was no significant pressure applied to the muscle. The probe was held by a fixture, as presented in FIG. 1. The second measurement was obtained by attaching one of the weights to the probe, and loosening the probe fixture, allowing the probe to slide vertically while maintaining a vertical orientation, such that the pressure was applied normal to the tissue surface. Each spectrum was acquired within 5 seconds of the application of pressure. Subsequently, the probe was removed from the muscle, and at least a 30 second time delay was allowed for the tissue to return to its normal state prior to a subsequent measurement. The set was then repeated at a different location on the muscle, with a different pressure until all five weights were used. The order of the pressure applied was randomized on each muscle; therefore, it is assumed that the influence of the previously applied pressure on each measurement is negligible. In total, there were 19 measurements per specified pressure, and 95 (19 muscles×5 sets) measurements with no pressure applied.

The repeatability of the amount of pressure applied to the tissue was tested by placing the setup over a scale (in place of the tissue) and measuring the weight. The pressure applied by each weight was measured five times, and the variation was determined to be less than 5%.

Each tissue measurement was analyzed by using Eqn. 1[58] as shown below. Briefly, the relative reflectance spectrum, $R^{Rel}_T(\lambda)$, is obtained from the ratio of the tissue spectrum, $I_T(\lambda)$, over the spectrum obtained with a spectrally-flat diffuse reflector (Labsphere, Spectralon), denoted as $I_R(\lambda)$. The amplitude of $I_R(\lambda)$ is dependent on the distance between a probe and the diffuse reflector. This distance is difficult to control with sub-millimeter resolution; therefore, the spectrum is normalized at 610 nm so that its amplitude is independent of the distance between the probe and the diffuse reflector. Finally, the spectrum is referenced by the spectrum obtained from a liquid calibration medium with known optical properties ($I_C(\lambda_0)$) at $\lambda_0=610$ nm. The calibration medium was a suspension of 0.16 grams of titanium dioxide powder (J. T. Baker) in 200 ml of deionized water.

$$R_T^{Rel}(\lambda) = \frac{I_T(\lambda)}{I_R(\lambda)} \frac{I_R(\lambda_0)}{I_C(\lambda_0)} \quad (1)$$

$$= a\mu_s'(\lambda)\exp\left(-C_{corr}(\lambda)\mu_a(\lambda)\frac{b}{(C_{corr}(\lambda)\mu_a(\lambda)\mu_s'(\lambda))^c}\right)$$

The absorption and reduced scattering coefficients of the tissue are denoted by $\mu_a(\lambda)$ and $\mu_s'(\lambda)$, respectively, and the values of a, b and c were determined to be 0.11, 0.22 and 0.2, respectively, as described in Reif et. al[58]. Given that the primary absorbers, oxy- and deoxy-hemoglobin, are compartmentalized in blood vessels, a correction factor ($C_{corr}$) for the inhomogeneous distribution of the absorption has been applied, as derived by other groups[55,59,60]. The correction factor, given by Eqn. 2, assumes that hemoglobin is concentrated in blood vessels which are modeled as infinitely long cylinders.

$$C_{corr}(\lambda) = \left\{\frac{1-\exp[-2\mu_{a,bl}(\lambda)r]}{2\mu_{a,bl}(\lambda)r}\right\} \quad (2)$$

The mean value of the blood vessel radius is given by r and the absorption coefficient of whole blood is given by $\mu_{a,bl}(\lambda)$[55,59,60].

The reduced scattering and absorption coefficients have been modeled by equations 3 and 4 respectively:

$$\mu_s'(\lambda) = d\cdot\lambda^{-e} \quad (3)$$

$$\mu_a(\lambda) = f_1(f_2\epsilon_{HbO}(\lambda) + (1-f_2)\epsilon_{Hb}(\lambda)) \quad (4)$$

where $\epsilon_{HbO}$ and $\epsilon_{Hb}$ are the extinction coefficients of oxy- and deoxy-hemoglobin, respectively.

Five coefficients are obtained from the model: blood volume fraction ($f_1$); hemoglobin oxygen saturation ($f_2$); blood vessel radius (r); and the reduced scattering coefficient, $\mu_s'$, which are described by the exponent of the power law or Mie-theory slope (e); and since the value d has no physical meaning, and its units depend directly on e such that the units of $\mu_s'$ are in inverse length (i.e. cm$^{-1}$), the value of $\mu_s'$ is described at 700 nm ($\mu_s'(700\text{ nm}) = d\cdot 700^{-e}$), as defined by Eqn. 3. The Mie slope is a constant, which can be related to the mean size of the scattering particles, and can have a value between 0.37 (particles much larger than the wavelength of the light) and 4 (particles much smaller than the wavelength of the light; also known as Rayleigh scattering)[61]. The blood volume fraction is calculated by assuming a blood hemoglobin concentration of 150 g/l, which is typical for whole blood.

The model described by Equation 1 was fit to the relative reflectance spectrum where d, e, $f_1$, $f_2$ and r are fitting parameters. A least-squares fit with a Levenberg-Marquardt algorithm was implemented with Matlab, and the parameters had the following constraints: d, r $\geq$ 0; 0.37 $\leq$ e $\leq$ 4 and 0 $\leq$ $f_1$, $f_2$ $\leq$ 1. The starting point for all the parameters was the lowest value of the constraint. Other starting points were tested and the values for the parameters obtained converged; therefore, it can be assumed that the solution is unique. FIG. 2a shows an example of the relative reflectance and of the model fit at two different probe pressures. It can be readily noted that a degree of desaturation is exhibited in the trace taken at 0.2 N/mm$^{50}$, compared with the trace at zero pressure. The values for $\mu_s'(700\text{ nm})$, e, $f_1$, $f_2$ and r obtained in FIG. 2a with a pressure of 0 N/mm$^{50}$ were 7.21 cm$^{-1}$, 0.88, 0.8%, 90% and 3.8 μm, respectively; and with a pressure of 0.2 N/mm$^{50}$ were 10.6 cm$^{-1}$, 0.85, 0.5%, 41% and 1.1 μm, respectively.

The mean and standard deviations of the five parameters extracted from the model are presented in FIGS. 11b through 11f. By observation, the data follow a linear or exponential relationship with pressure; therefore, the mean value of each parameter has been modeled as a function of the probe pressure with an exponential expression given by Eqn. 5:

$$y = a_0 + a_1\exp(a_2\cdot P) \quad (5)$$

where $a_0$, $a_1$ and $a_2$ are fitting coefficients, and P is the probe pressure. The results from the exponential fits are plotted as the solid lines in FIGS. 2b through 2f.

The blood vessel radius, oxygen saturation and Mie-theory slope decrease with pressure, while the reduced scattering coefficient at 700 nm increases as a function of pressure. It is hypothesized that the pressure applied by the probe compresses the blood vessels, consequently reducing the blood flow. This would explain the decrease in the blood vessel radius and the desaturation of the blood due to the tissue oxygen consumption and disruption of the flow of oxygenated blood arriving to the tissue. The probe pressure might also increase the density of scatterers per unit volume, which would be consistent with the increase in reduced scattering coefficient. The decrease in Mie slope is an indication that the scattering is mostly due to larger particles, which could be a consequence of increasing the density of large organelles per unit volume. The mean blood volume fraction varies less than 20% for the range of pressures applied and does not seem to follow a trend; therefore, it can be assumed that the blood volume fraction is not dependent on the probe pressure. It is important to note that the dominant contributors to the optical absorption in muscle come from hemoglobin and myoglobin. The absorption spectrum of myoglobin is very similar to that of hemoglobin and its concentration in muscles is typically lower than that of hemoglobin[62,63], therefore its contribution to the optical absorption has been neglected in this paper. Although the blood volume is reduced when the blood vessels are compressed, the concentration of myoglobin might increase counteracting the decrease in hemoglobin absorption. If so, the model would fit the absorption spectra of hemoglobin to myoglobin which would explain the lack of change in the blood volume fraction.

In conclusion, the amount of probe pressure applied on the thigh muscle affects the reflectance spectrum in a predictable manner. Therefore, it is hypothesized that by limiting or controlling the probe pressure it would be possible to reduce the spectral variability in reflectance measurements, and increase the sensitivity and specificity of several studies for early cancer diagnosis. An analytical model was fit to the reflectance spectra to extract five parameters, which provide a basic physiological description for the change in the relative reflectance spectra. All these parameters, with the exception of the blood volume fraction, vary as a function of the probe pressure.

In certain embodiments, the devices described herein can be modified to use other methods, besides optical fibers, to transmit and collect light that is at an angle with the normal of the tissue interface. Optionally, a single fiber optic probe can be used as both the source and the collection fiber, or a combination or one or more sources and collectors can be used. The optical fibers do not need to be completely parallel to each other. The optical fibers can have a variety of diameters, numerical apertures and separations. The system could be used to also measure superficial fluorescent signal.

REFERENCE LIST

1) I. J. Bigio and J. R. Mourant, "Ultraviolet and visible spectroscopies for tissue diagnostics: fluorescence spectroscopy and elastic-scattering spectroscopy," *Phys. Med. Biol.* 42, 803-814 (1997)

2) O. A'Amar, R. D. Ley and I. J. Bigio, "Comparison between ultraviolet-visible and near-infrared elastic scattering spectroscopy of chemically induced melanomas in an animal model," *J. Biomed. Opt.* 9, 1320-1326, (2004)
3) I. J. Bigio and S. G. Bown, "Spectroscopic sensing of cancer and cancer chemotherapy, current status of translational research," *Cancer Biol. Ther.* 3, 259-267 (2004)
4) T. J. Farrell, M. S. Patterson, and B. C. Wilson, "A diffusion theory model of spatially-resolved, steady-state diffuse reflectance for the non-invasive determination of tissue optical properties in vivo," *Med. Phys.* 19, 879-888 (1992)
5) A. Kienle and M. S. Patterson, "Improved solutions of the steady-state and the time-resolved diffusion equations for reflectance from a semi-infinite turbid medium," *J. Opt. Soc. Am. A* 14, 246-254 (1997)
6) R. M. P. Doombos, R. Lang, M. C. Aalders, F. W. Cross, and H. J. C. M. Sterenborg, "The determination of in vivo human tissue optical properties and absolute chromophore concentrations using spatially resolved steady-state diffuse reflectance spectroscopy," *Phys. Med. Biol.* 44, 967-981 (1991)
7) G. Zonios and A. Dimou, "Modeling diffuse reflectance from semi-infinite turbid media: application to the study of skin optical properties," *Opt. Exp.* 14, 8661-8674 (2006)
8) M. Johns, C. A. Giller, D. C. German and H. Liu, "Determination of reduced scattering coefficient of biological tissue from a needle-like probe," *Opt. Exp.* 13, 4828-4842 (2005)
9) F. Bevilacqua and C. Depeursinge, "Monte Carlo study of diffuse reflectance at source-detector separations close to one transport mean free path," *J. Opt. Soc. Am. A* 16, 2935-2945 (1999)
10) A. Amelink, H. J. C. M. Sterenborg, M. P. L. Bard and S. A. Burgers, "In vivo measurement of the optical properties of tissue by use of differential path-length spectroscopy," *Opt. Lett.* 29, 1087-1089 (2004)
11) A. Amelink and H. J. C. M. Sterenborg, "Measurement of the local optical properties of turbid media by differential path-length spectroscopy," *Appl. Opt.* 43, 3048-3054 (2004)
12) T. P. Moffitt and S. A. Prahl, "Sized-fiber reflectometry for measuring local optical properties," *Selected Topics in Quantum Electronics, IEEE Journal of,* 7, 952-958 (2001)
13) F. Bevilacqua, D. Piguet, P. Marquet, J. D. Gross, B. J. Tromberg and C. Depeursinge, "In vivo local determination of tissue optical properties: applications to human brain," *Appl. Opt.,* 38, 4939-4950 (1999)
14) C. K. Hayakawa, J. Spanier, F. Bevilacqua, A. K. Dunn, J. S. You, B. J. Tromberg, V. Venugopalan, "Perturbation Monte Carlo methods to solve inverse photon migration problems in heterogeneous tissues," *Opt. Lett.,* 26, 1335-1337 (2001)
15) C. K. Hayakawa, B. Y. Hill, J. S. You, F. Bevilacqua, J. Spanier, and V. Venugopalan, "Use of the delta-P1 Approximation for Recovery of Optical Absorption, Scattering, and Asymmetry Coefficients in Turbid Media," *Appl. Opt.* 43, 4677-4684 (2004)
16) Q. Liu and N. Ramanujam, "Sequential estimation of optical properties of a two-layered epithelial tissue model from depth-resolved ultraviolet-visible diffuse reflectance spectra," *Appl. Opt.,* 45, 4776-4790 (2006)
17) G. M. Palmer and N. Ramanujam, "A Monte Carlo based inverse model for calculating tissue optical properties, part I: theory and validation on synthetic media, *Appl. Opt.,* 45, 1062-1071 (2006)
18) G. M. Palmer, C. Zhu, T. M. Breslin, F. Xu, K. W. Gilchrist and N. Ramanujam, "A Monte Carlo based inverse model for calculating tissue optical properties, part II: application to breast cancer diagnosis," *Appl. Opt.,* 45, 1072-1078 (2006)
19) T. J. Pfefer, L. S. Matchette, C. L. Bennett, J. A. Gall, J. N. Wilke, A. Durkin and M. N. Ediger, "Reflectance-based determination of optical properties in highly attenuating tissue," *J. Biomed. Opt.,* 8, 206-215 (2003)
20) G. Zonios, L. T. Perelman, V. Backman, R. Manoharan, M. Fitzmaurice, J. Van Dam, and M. S. Feld, "Diffuse reflectance spectroscopy of human adenomatous colon polyps in vivo," *Appl. Opt.* 38, 6628-6637 (1999)
21) J. Sun, K. Fu, A. Wang, A. W. H. Lin, U. Utzinger, and R. Drezek, "Influence of fiber optic probe geometry on the applicability of inverse models of tissue reflectance spectroscopy: computational models and experimental measurements," *Appl. Opt.* 45, 8152-8162 (2006)
22) U. Utzinger and R. Richards-Kortum, "Fiber optic probes for biomedical optical spectroscopy," *J. Biomed. Opt.,* 8, 121-147 (2003)
23) A. Myakov, L. Nieman, L. Wicky, U. Utzinger, R. Richards-Kortum and K. Sokolov, "Fiber optic probe for polarized reflectance spectroscopy in vivo: Design and performance," *J. Biomed. Opt.,* 7, 388-397 (2002)
24) C. Xhu, Q. Liu and N. Ramanujam, "Effect of fiber optic probe geometry on depth-resolved fluorescence measurements from epithelial tissues: a Monte Carlo simulation," *J. Biomed. Opt.,* 8, 237-247 (2003)
25) T. J. Pfefer, K. T. Schomacker, M. N. Ediger and N. S. Nishioka, "Multiple-fiber probe design for fluorescence spectroscopy in tissue," *Appl. Opt.,* 41, 4712-4721 (2002)
26) A. Wang, J. Bender, U. Utzinger and R. Drezek, "Depth-sensitive reflectance measurements using obliquely oriented fiber probes," *J. Biomed. Opt,* 10, 044017 (2005)
27) L. Nieman, A. Myakov, J. Aaron and K. Sokolov, "Optical sectioning using a fiber probe with an angled illumination-collection geometry: evaluation in engineered tissue media," *Appl. Opt.,* 43, 1308-1319 (2004)
28) J. Pfefer, A. Agrawal and R. Drezek, "Oblique-incidence illumination and collection for depth-selective fluorescence spectroscopy," *J. Biomed. Opt.,* 10, 044016 (2005)
29) S. P. Lin, L. Wang, S. L. Jacques, F. K. Tittel, "Measurement of tissue optical properties by the use of oblique-incidence optical fiber reflectometry," *Appl. Opt.,* 36, 136-143 (1997)
30) D. Arifler, R. A. Schwarz, S. K. Chang and R. Richards-Kortum, "Reflectance spectroscopy for diagnosis of epithelial precancer: model-based analysis of fiber-optic probe designs to resolve spectral information from epithelium and stroma," *Appl. Opt.,* 44, 4291-4305 (2005)
31) S. L. Jacques and L. Wang, "Monte Carlo modeling of light transport in tissue," Optical-Thermal Response of Laser Irradiated Tissue ed. A. J. Welch and M. J. C. van Gemert (New York: Plenum), 73-100 (1995)
32) L. H. Wang, S. L. Jacques and L. Zheng, "MCML: Monte-Carlo modeling of light transport in multilayered tissues," *Comput. Methods Programs Biomed.* 47, 131-146 (1995)
33) M. Hiraoka, M. Firbank, M. Essenpreis, M. Cope, S. R. Arridge, P. van der Zee, and D. T. Delpy, "A Monte Carlo investigation of optical path-length in inhomogeneous tissue and its application to near-infrared spectroscopy," *Phys. Med. Biol.* 38, 1859-1876 (1993)
34) L. G. Henyey and J. L. Greenstein, "Diffuse radiation in the galaxy," *Astrophys. J* 93, 70-83 (1941)
35) P. Thueler, I. Charvet, F. Bevilacqua, M. St. Ghislain, G. Ory, P. Marquet, P. Meda, B. Vermeulen and C. Depeursinge, "In vivo endoscopic tissue diagnostics based on spectroscopic absorption, scattering and phase function properties," *J. Biomed. Opt.* 8, 495-503 (2003)

36) S. T. Flock, S. L. Jacques, B. C. Wilson, W. M. Star, M. J. C. van Germet, "Optical properties of Intralipid: a phantom medium for light propagation studies," *Lasers Surg. Med.* 12, 510-519 (1992)

37) M. G. Nichols, E. L. Hull and T. H. Foster, "Design and testing of a white-light, steady-state diffuse reflectance spectrometer for determination of optical properties of highly scattering systems," *Appl. Opt.* 36, 93-104 (1997)

38) M. Firbank and D. T. Delpy, "A design for a stable and reproducible phantom for use in near infra-red imaging and spectroscopy," *Phys. Med. Biol.* 38, 847-853 (1993)

39) W. F. Cheong, S. A. Prahl and A. J. Welch, "A review of the Optical Properties of Biological Tissues," *IEEE J. of Quan. Elec.* 26, 2166-2185 (1990)

40) A. Sassaroli and S. Fantini, "Comment on the modified Beer-Lambert law for scattering media," *Phys. Med. Biol.* 49, N255-N257 (2004)

41) C. F. Bohren and D. R. Huffman, "Absorption and scattering of light by small particles," (1983)

42) J. R. Mourant, J. Boyer, A. H. Hielscher and I. J. Bigio, "Influence of the phase function on light transport measurements in turbid media performed with small source-detector separations," *Opt. Lett.* 21, 546-548 (1996)

43) M. Canpolat and J. R. Mourant, "High-angle scattering events strongly affect light collection in clinically relevant measurement geometries for light transport through tissue," *Phys. Med. Biol.* 45, 1127-1140 (2000)

44) M. Canpolat and J. R. Mourant, "Particle size analysis of turbid media with a single optical fiber in contact with the medium to deliver and detect white light," *Appl. Opt.* 40, 3792-3799 (2001)

45) L. T. Perelman, V. Backman, M. Wallace, G. Zonios, R. Manoharan, A. Nusrat, S. Shields, M. Seiler, C. Lima, T. Hamano, I. Itzkan, J. Van Dam, J. M. Crawford, and M. S. Feld, "Observation of periodic fine structure in reflectance from biological tissue: a new technique for measuring nuclear size distribution," *Phys. Rev. Lett.* 80, 627-630 (1998)

46) A. Dunn and D. Boas, "Transport-based image reconstruction in turbid media with small source-detector separations," *Opt. Lett.* 25, 1777-1779 (2000)

47) P. R. Bargo, S. A. Prahl, S. L. Jacques, "Collection efficiency of single optical fiber in turbid media," *Appl. Opt.* 42, 3187-3197 (2003)

48) J. R. Mourant, J. P. Freyer, A. H. Hielscher, A. A. Eick, D. Shen, and T. M. Johnson, "Mechanisms of light scattering from biological cells relevant to noninvasive optical-tissue diagnostics," *Appl. Opt.* 37, 3586-3593 (1998)

49) G. Zonios, L. T. Perelman, V. Backman, R. Manoharan, M. Fitzmaurice, J. Van Dam and M. S. Feld, "Diffuse reflectance spectroscopy of human adenomatous colon polyps in vivo," Appl. Opt. 38(31), 6628-6637 (1999)

50) G. Zonios and Aikaterini Dimou, "Modeling diffuse reflectance from semi-infinite turbid media: application to the study of skin optical properties," *Opt. Express* 14, 8661-8674 (2006)

51) M. Johns, C. Giller, D. German, and H. Liu, "Determination of reduced scattering coefficient of biological tissue from a needle-like probe," *Opt. Express* 13, 4828-4842 (2005)

52) Y. N. Mirabal, S. K. Chang, E. N. Atkinson, A. Malpica, M. Follen, R. Richards-Kortum, "Reflectance spectroscopy for in vivo detection of cervical precancer," *J. Biomed. Opt.* 7(4), 587-594 (2002)

53) L. B. Lovat, K. Johnson, G. D. Mackenzie, B. R. Clark, M. R. Novelli, S. Davies, M. O'Donovan, C. Selvasekar, S. M. Thorpe, D. Pickard, R. Fitzgerald, T. Feam, I. Bigio and S. G. Bown, "Elastic scattering spectroscopy accurately detects high grade dysplasia and cancer in Barrett's oesophagus," Gut 55, 1078-1083 (2006)

54) 1. J. Bigio, 0. A'Amar and M. S. Hirsch, "Elastic scattering spectroscopy for detection of prostate cancer: preliminary feasibility study," Diagnostic Optical Spectroscopy in Biomedicine II, Proc. SPIE 5141: 142-146 (2003)

55) A. Amelink, H. J. C. M Sterenborg, M. P. L. Bard and S. A. Burgers, "In vivo measurements of the local optical properties of tissue by use of differential path-length spectroscopy," *Opt. Lett.* 29(10), 1087-1089 (2004)

56) H. Shangguan, S. A. Prahl, S. L. Jacques and L. W. Casperson, "Pressure effects on soft tissues monitored by changes in tissue optical properties," in Laser-Tissue Interaction IX, S. L. Jacques Ed., Proc. SPIE 3254, 366-371 (1998)

57) Nath, K. Rivoire, S. Chang, D. Cox, E. N. Atkinson, M. Follen, R. Richards-Kortum, "Effect of probe pressure on cervical fluorescence spectroscopy measurements," *J. Biomed. Opt.* 9(3), 523-533 (2004)

58) Reif R., A'Amar O. and Bigio I. J., "Analytical model of light reflectance for extraction of the optical properties in small volumes of turbid media," Appl. Opt. 46(29), 7317-7328 (2007)

59) R. L. P. van Veen, W. Verkruysse and H. J. C. M. Sterenborg, "Diffuse-reflectance spectroscopy from 500 to 1060 nm by correction of inhomogeneously distributed absorbers," *Opt. Letters* 27, 246-248 (2002)

60) L. O. Svaasand, E. J. Fiskerstrand, G. Kopstad, L. T. Norvang, E. K. Svaasand, J. S. Nelson and M. W. Berns, "Therapeutic response during pulsed laser treatment of port-wine stains: dependence on vessel diameter and depth in dermis," *Lasers Med. Sci.* 10, 235-243 (1995)

61) J. R. Mourant, T. Fuselier, J. Boyer, T. M. Johnson and I. J. Bigio, "Predictions and measurements of scattering and absorption over broad wavelength ranges in tissue media," Appl. Opt. 36, 949-957 (1997)

62) P. J. O'Brien, H. Shen, L. J. McCutcheon, M. O'Grady, P. J. Byrne, H. W. Ferguson, M. S. Mirsalimi, R. J. Julian, J. M. Sargeant, R. R. M. Tremblay and T. E. Blackwell, "Rapid, simple and sensitive microassay for skeletal and cardiac muscle myoglobin and hemoglobin: use in various animals indicates functional role of myohemoproteins," Mol. Cell. Biochem. 112, 45-52 (1992)

63) C. Casavola, L. A. Paunescu, S. Fantini and E. Gratton, "Blood flow and oxygen consumption with near-infrared spectroscopy and venous occlusion: spatial maps and the effect of time and pressure inflation," *J. Biomed. Opt.* 5, 269-276 (2000)

All references cited herein are incorporated in their entirety by reference herein.

TABLE 1

| | | Fiber Tilt Angle | | | |
|---|---|---|---|---|---|
| | | 0 | 15 | 30 | 45 |
| a | MC | 1.2E−05 | 1.1E−05 | 1.1E−05 | 1.0E−05 |
| | Experiment | 0.11 | 0.11 | 0.11 | 0.10 |
| $a_0$ | MC | 0.0E−05 | 0.0E−05 | 0.0E−05 | 0.0E−05 |
| | Experiment | −0.04 | −0.04 | −0.03 | −0.01 |

TABLE 2

|  |  | Fiber Tilt Angle | | | |
| --- | --- | --- | --- | --- | --- |
|  |  | 0 | 15 | 30 | 45 |
| MC | μs' = 5 | 0.33 | 0.32 | 0.32 | 0.32 |
|  | μs' = 10 | 0.33 | 0.31 | 0.31 | 0.29 |
|  | μs' = 20 | 0.30 | 0.30 | 0.30 | 0.28 |
|  | Mean | 0.32 | 0.31 | 0.31 | 0.30 |
| Experiment | μs' = 5.5 | 0.20 | 0.26 | 0.25 | 0.26 |
|  | μs' = 10.6 | 0.22 | 0.25 | 0.25 | 0.25 |
|  | μs' = 20.7 | 0.23 | 0.25 | 0.23 | 0.24 |
|  | Mean | 0.22 | 0.25 | 0.24 | 0.25 |

TABLE 3

|  |  | Fiber Tilt Angle | | | |
| --- | --- | --- | --- | --- | --- |
|  |  | 0 | 15 | 30 | 45 |
| MC | μs' = 5 | 0.21 | 0.21 | 0.21 | 0.20 |
|  | μs' = 10 | 0.21 | 0.22 | 0.21 | 0.19 |
|  | μs' = 20 | 0.20 | 0.20 | 0.20 | 0.19 |
|  | Mean | 0.21 | 0.21 | 0.21 | 0.19 |
| Experiment | μs' = 5.5 | 0.20 | 0.20 | 0.20 | 0.20 |
|  | μs' = 10.6 | 0.20 | 0.20 | 0.20 | 0.20 |
|  | μs' = 20.7 | 0.20 | 0.20 | 0.20 | 0.20 |
|  | Mean | 0.20 | 0.20 | 0.20 | 0.20 |

TABLE 4

|  |  | COLUMNS | | | | | | | |
| --- | --- | --- | --- | --- | --- | --- | --- | --- | --- |
|  |  | A | B | C | D | E | F | G | H |
| PARAMETERS | $n_f$ | 1.5 | 1.46 | 1.5 | 1.5 | 1.5 | 1.5 | 1.5 | 1.5 |
|  | $n_m$ | 1.4 | 1.33 | 1.4 | 1.4 | 1.4 | 1.4 | 1.4 | 1.4 |
|  | Separation (μm) | 250 | 250 | 200 | 250 | 250 | 250 | 250 | 250 |
|  | Phase Function | HG | HG | HG | MHG | HG | HG | HG | HG |
|  | g | 0.9 | 0.9 | 0.9 | 0.9 | 0.2 | 0.5 | 0.75 | 0.95 |
| TILT ANGLE |  |  |  |  |  |  |  |  |  |
| 0 | a | 1.2E−05 | 1.2E−05 | 1.4E−05 | 1.2E−05 | 1.1E−05 | 1.1E−05 | 1.2E−05 | 1.2E−05 |
|  | $a_0$ | 0.0E−05 | 0.0E−05 | 0.0E−05 | 1.5E−05 | 4.8E−05 | 1.7E−05 | 0.0E−05 | 0.0E−05 |
|  | b | 0.32 | 0.30 | 0.26 | 0.31 | 0.36 | 0.32 | 0.31 | 0.31 |
|  | c | 0.21 | 0.21 | 0.21 | 0.21 | 0.20 | 0.20 | 0.20 | 0.19 |
| 45 | a | 1.0E−05 | 1.1E−05 | 1.3E−05 | 1.0E−05 | 9.9E−06 | 1.0E−05 | 1.1E−05 | 1.0E−05 |
|  | $a_0$ | 0.0E−05 | 0.0E−05 | 0.0E−05 | 2.1E−05 | 4.0E−05 | 2.0E−05 | 0.0E−05 | 0.0E−05 |
|  | b | 0.30 | 0.30 | 0.25 | 0.30 | 0.35 | 0.32 | 0.30 | 0.30 |
|  | c | 0.19 | 0.20 | 0.20 | 0.20 | 0.20 | 0.21 | 0.21 | 0.21 |

TABLE 5

|  |  | Fiber Tilt Angle | | | |
| --- | --- | --- | --- | --- | --- |
| Actual $\mu_a$ | Actual $\mu_s'$ | 0 | 15 | 30 | 45 |
| 0 | 9.2 | 0.00 ± 0.00 | 0.00 ± 0.00 | 0.00 ± 0.00 | 0.00 ± 0.00 |
|  | 17.5 | 0.00 ± 0.00 | 0.00 ± 0.00 | 0.00 ± 0.00 | 0.00 ± 0.00 |
| 0.5 | 9.2 | 0.58 ± 0.03 | 0.58 ± 0.01 | 0.49 ± 0.00 | 0.58 ± 0.02 |
|  | 17.5 | 0.58 ± 0.02 | 0.58 ± 0.02 | 0.49 ± 0.02 | 0.53 ± 0.02 |
| 2.8 | 9.2 | 2.71 ± 0.04 | 3.18 ± 0.03 | 2.62 ± 0.02 | 2.89 ± 0.04 |
|  | 17.5 | 2.70 ± 0.04 | 3.10 ± 0.02 | 2.45 ± 0.14 | 2.82 ± 0.03 |
| 8.5 | 9.2 | 7.98 ± 0.14 | 8.75 ± 0.12 | 8.01 ± 0.16 | 8.53 ± 0.19 |
|  | 17.5 | 8.39 ± 0.06 | 8.56 ± 0.52 | 8.23 ± 0.05 | 8.57 ± 0.08 |

The units are in cm$^{-1}$

TABLE 6

|  |  | Fiber Tilt Angle | | | |
| --- | --- | --- | --- | --- | --- |
| Actual $\mu_s'$ | Actual $\mu_a$ | 0 | 15 | 30 | 45 |
| 9.2 | 0 | 8.7 ± 0.3 | 8.8 ± 0.1 | 9.1 ± 0.1 | 9.6 ± 0.1 |
|  | 0.5 | 9.0 ± 0.3 | 9.6 ± 0.1 | 9.0 ± 0.1 | 9.1 ± 0.2 |
|  | 2.8 | 8.5 ± 0.3 | 9.5 ± 0.2 | 9.7 ± 0.0 | 9.2 ± 0.3 |
|  | 8.5 | 9.3 ± 0.3 | 9.6 ± 0.2 | 9.3 ± 0.1 | 8.8 ± 0.3 |
| 17.5 | 0 | 16.9 ± 1.1 | 17.4 ± 0.5 | 17.4 ± 0.2 | 18.3 ± 0.6 |
|  | 0.5 | 17.4 ± 0.9 | 19.0 ± 1.0 | 17.3 ± 0.2 | 17.3 ± 0.9 |
|  | 2.8 | 16.4 ± 0.7 | 18.4 ± 0.4 | 17.6 ± 1.1 | 18.3 ± 0.4 |
|  | 8.5 | 18.5 ± 0.4 | 17.1 ± 2.0 | 17.2 ± 0.2 | 16.4 ± 0.4 |

The units are in cm$^{-1}$

The invention claimed is:

1. A device for measuring light scattering and absorption properties of a tissue, the device comprising:
a probe having proximal and distal ends, said probe comprising first and second optical fibers, wherein said first optical fiber is operatively connected to a light source, and said second optical fiber is operatively connected to an optical detector, wherein said first and said second optical fibers are substantially parallel to each other at said distal end, and are separated at said distal end by a distance of less than 2 mm, wherein said first and second optical fibers are arranged in said probe at an angle, θ=10° to 45°, to the plane perpendicular to the distal end of said probe and wherein the tips of the optical fibers at the distal end are polished such that they are parallel to the surface of a probed medium; and a computer-readable medium comprising instructions for obtaining an absolute reflectance value from a measured reflectance spectrum, the medium comprising:

a) instructions for receiving a value for measured light energy from a turbid medium of interest;

b) instructions for receiving values for measured light energy from a calibration turbid medium of known reflectance and absorption properties;

c) instructions for calculating an absolute reflectance value, R, at a given wavelength, for said turbid medium of interest, said instructions comprising applying the values received according to instructions (a) and (b) to the relationship of Equation (1)

$$R = \frac{S_P(\lambda)}{S_C(\lambda)} R_C(\lambda) \quad \text{Equation (1)}$$

wherein $S_p(\lambda)$ is the reflected light energy detected from the turbid medium, $S_c(\lambda)$ is the reflected light energy detected from a turbid medium with known reduced scattering and/or absorption coefficients, and $R_c(\lambda)$ is the reflectance from said turbid medium with known reduced scattering and/or absorption coefficients;

d) instructions for determining absorption and/or reduced scattering coefficients for said turbid medium of interest by applying the relationship of Equation (2) to said absolute reflectance value, R $$R = (a\mu_s')\exp\left(-\mu_a \frac{b}{(\mu_a\mu_s')^c}\right) \quad \text{Equation (2)}$$

wherein a, b, and c are constants, $\mu_s'$ is the reduced scattering coefficient of said turbid medium of interest, and $\mu_a$ is the absorption coefficient of said turbid medium of interest; and e) instructions for transmitting a value of R, $\mu_s'$ and/or $\mu_a$ to an output device.

2. The device of claim 1, wherein said probe comprises an endoscopic probe.

3. The device of claim 1, wherein said first and second optical fibers are separated by less than or equal to 700 μm at the distal end of said probe.

4. A method of obtaining an absolute value for reflectance, and/or a reduced scattering coefficient and/or an absorption coefficient from spectra reflected from a turbid medium of interest, the method comprising:

a) irradiating a first turbid medium with light energy from a source in contact with a first turbid medium, said first turbid medium having known reduced scattering and absorption coefficients;

b) for said first turbid medium, measuring an amount of light energy reflected from said source to a detector;

c) irradiating a turbid medium of interest with light energy from a source in contact with said turbid medium of interest;

d) collecting and detecting the amount of light energy from said source that is reflected to a detector from said turbid medium of interest, e) applying measured data representing the amounts of light energy reflected from said first turbid medium having known reduced scattering and absorption coefficients, and measured data representing the amount of light energy reflected from said turbid medium of interest to Equation (1):

$$R = \frac{S_P(\lambda)}{S_C(\lambda)} R_C(\lambda) \quad \text{Equation (1)}$$

wherein $S_p(\lambda)$ is the reflected light spectra detected from the turbid medium of interest, $S_c(\lambda)$ is the reflected light spectra detected from said turbid medium with known reduced scattering and/or absorption coefficients, $R_c(\lambda)$ is the reflectance from said first turbid medium with known reduced scattering and/or absorption coefficients, wherein an absolute value for the reflectance, R, from said turbid medium of interest is obtained;

f) repeating steps a-e at a second, different wavelength of light; and g) determining a reduced scattering coefficient and/or an absorption coefficient for said turbid medium of interest, wherein said determining comprises applying Equation (2) to said absolute reflectance value, R $$R = (a\mu_s')\exp\left(-\mu_a \frac{b}{(\mu_a\mu_s')^c}\right) \quad \text{Equation (2)}$$

wherein a, b, and c are constants, $\mu_s'$ is the reduced scattering coefficient, and $\mu_a$ is the absorption coefficient, whereby an absolute value for reflectance, a reduced scattering coefficient and/or an absorption coefficient are determined from said turbid medium of interest.

5. The method of claim 4, wherein said turbid medium is a tissue.

6. The method of claim 4, wherein said tissue is an epithelial layer.

7. The method of claim 4, further comprising the step of comparing said absolute reflectance value, R, to an absolute reflectance value obtained from a reference turbid medium, wherein a difference between said absolute reflectance values is indicative of a difference between said turbid medium of interest and said reference turbid medium.

8. The method of claim 4, further comprising the step of comparing an absolute value for the reduced scattering or absorption coefficient of said turbid medium of interest to a reduced scattering coefficient and/or absorption coefficient obtained from a reference turbid medium, wherein a difference in said absolute value is indicative of a difference between said turbid medium of interest and said reference turbid medium.

9. The method of claim 8, wherein said turbid medium of interest and said reference turbid medium are each an epithelial layer, and wherein a difference in said absolute value is indicative of a disease state.

10. The method of claim 4, wherein the data permitting the obtaining of the absolute value for the reflectance from spectra reflected from a turbid medium of interest are obtained using a device comprising: a probe having proximal and distal ends, said probe comprising first and second optical fibers, wherein said first optical fiber is operatively connected to a light source, and said second optical fiber is operatively connected to an optical detector, wherein said first and said second optical fibers are substantially parallel to each other at said distal end, and are separated at said distal end by a distance of less than 2 mm, wherein said first and second optical fibers are arranged in said probe at an angle, θ=10° to 45°, to the plane perpendicular to the distal end of said probe and wherein the tips of the optical fibers at the distal end are polished such that they are parallel to the surface of a probed medium.

11. A method of determining a reduced scattering coefficient and/or an absorption coefficient from a turbid medium of interest, the method comprising a) obtaining reflectance spectra from a turbid medium of interest using a probe in contact with said turbid medium of interest, said probe operatively connected to a light energy source which irradiates said turbid medium of interest and an optical detector which detects light energy reflected from said turbid medium of interest, and standardizing said reflectance data with reference data obtained by applying Equation (1) to reflectance data obtained from a calibrating turbid medium having known values of absorption and/or reduced scattering coefficient, $$R = \frac{S_P(\lambda)}{S_C(\lambda)} R_C(\lambda) \quad \text{Equation (1)}$$

wherein $S_p(\lambda)$ is the reflected light spectra detected from the turbid medium, $S_c(\lambda)$ is the reflected light spectra detected from a calibrating turbid medium with known reduced scattering and/or absorption coefficients, $R_c(\lambda)$ is the reflectance from said calibrating turbid medium with known reduced scattering and/or absorption coefficients; and wherein said standardizing provides absolute values for said reflectance spectra from measured reflectance spectra; and determining a reduced scattering coefficient and/or an absorption coefficient for said turbid medium of interest, wherein said determining comprises applying Equation (2) to said absolute reflectance value, R $$R = (a\mu'_s)\exp\left(-\mu_a \frac{b}{(\mu_a \mu'_s)^c}\right) \quad \text{Equation (2)}$$

wherein a, b, and c are constants, $\mu_s'$ is the reduced scattering coefficient of said turbid medium of interest, and $\mu_a$ is the absorption coefficient of said turbid medium of interest, whereby a reduced scattering coefficient and/or an absorption coefficient is determined for said turbid medium.

12. The method of claim 11, further comprising the step of comparing said absolute reflectance value, R, to an absolute reflectance value obtained from a reference turbid medium, wherein a difference between said absolute reflectance values is indicative of a difference between said turbid medium of interest and said reference turbid medium.

13. The method of claim 11, further comprising the step of comparing an absolute value for the reduced scattering or absorption coefficient of said turbid medium of interest to a reduced scattering coefficient and/or absorption coefficient obtained from a reference turbid medium, wherein a difference in said absolute value is indicative of a difference between said turbid medium of interest and said reference turbid medium.

14. A device for measuring light scattering and absorption properties of a tissue, the device comprising: a probe having proximal and distal ends, said probe comprising a) first and second optical fibers, wherein said first optical fiber is operatively connected to a light source, and said second optical fiber is operatively connected to an optical detector;

wherein said first and second optical fibers are substantially parallel to each other at said distal end, and are separated at said distal end by a distance of less than 2 mm;

and wherein the tips of the optical fibers at the distal end are polished such that they are parallel to the surface of a probed medium; and b) a computer-readable medium comprising instructions for obtaining an absolute reflectance value from a measured reflectance spectrum, the medium comprising:

instructions for receiving a value for measured light energy from a turbid medium of interest;

instructions for receiving values for measured light energy from a calibration turbid medium of known reflectance and absorption properties;

instructions for calculating an absolute reflectance value, R for said turbid medium of interest, said instructions comprising applying the values received according to instructions (a) and (b) to the relationship of Equation (1)

$$R = \frac{S_P(\lambda)}{S_C(\lambda)} R_C(\lambda) \quad \text{Equation (1)}$$

wherein $S_p(\lambda)$ is the reflected light energy detected from the turbid medium, $S_c(\lambda)$ is the reflected light energy detected from a turbid medium with known reduced scattering and/or absorption coefficients, and $R_c(\lambda)$ is the reflectance from said turbid medium with known reduced scattering and/or absorption coefficients; and instructions for transmitting a value for R to an output device, and the computer-readable medium further comprising instructions for determining absorption and/or reduced scattering coefficients for said turbid medium of interest by applying the relationship of Equation (2) to said absolute reflectance value, R $$R = (a\mu'_s)\exp\left(-\mu_a \frac{b}{(\mu_a \mu'_s)^c}\right) \quad \text{Equation (2)}$$

wherein a, b, and c are constants, $\mu_s'$ is the reduced scattering coefficient of said turbid medium of interest, and $\mu_a$ is the absorption coefficient of said turbid medium of interest; and instructions for transmitting a value of $\mu_s'$ and/or $\mu_a$ to an output device.

* * * * *